US011708378B2

(12) United States Patent
Shuttleworth et al.

(10) Patent No.: US 11,708,378 B2
(45) Date of Patent: *Jul. 25, 2023

(54) TRICYCLIC HETEROCYCLIC COMPOUNDS AS PHOSPHOINOSITIDE 3-KINASE INHIBITORS

(71) Applicant: Convalife (Shanghai) Co. Limited, Shanghai (CN)

(72) Inventors: Stephen Joseph Shuttleworth, Oxfordshire (GB); Alexander Richard Liam Cecil, Oxfordshire (GB); Franck Alexandre Silva, Oxfordshire (GB)

(73) Assignee: Convalife (Shanghai) Co. Limited, Shanghai (CN)

( * ) Notice: Subject to any disclaimer, the term of this patent is extended or adjusted under 35 U.S.C. 154(b) by 0 days.

This patent is subject to a terminal disclaimer.

(21) Appl. No.: 17/206,488

(22) Filed: Mar. 19, 2021

(65) Prior Publication Data

US 2022/0041624 A1 Feb. 10, 2022

Related U.S. Application Data

(63) Continuation of application No. 16/678,565, filed on Nov. 8, 2019, now abandoned, which is a continuation of application No. 15/961,404, filed on Apr. 24, 2018, now Pat. No. 10,513,530, which is a continuation of application No. 15/117,606, filed as application No. PCT/GB2015/050396 on Feb. 12, 2015, now Pat. No. 9,981,987.

(30) Foreign Application Priority Data

Feb. 12, 2014 (GB) ........................ 1402431

(51) Int. Cl.
C07D 519/00 (2006.01)
C07D 491/14 (2006.01)

(52) U.S. Cl.
CPC ......... *C07D 519/00* (2013.01); *C07D 491/14* (2013.01)

(58) Field of Classification Search
CPC ............................. C07D 519/00; C07D 491/14
See application file for complete search history.

(56) References Cited

U.S. PATENT DOCUMENTS

| 3,491,092 | A | 1/1970 | Grigat et al. |
| 4,017,500 | A | 4/1977 | Mayer et al. |
| 5,703,075 | A | 12/1997 | Gammill et al. |
| 7,182,958 | B1 | 2/2007 | Oren et al. |
| 7,361,662 | B2 | 4/2008 | Rault et al. |
| 8,242,116 | B2 | 8/2012 | Alexander et al. |

(Continued)

FOREIGN PATENT DOCUMENTS

| EP | 1277738 A1 | 1/2003 |
| EP | 1724267 A1 | 11/2006 |

(Continued)

OTHER PUBLICATIONS

U.S. Appl. No. 13/384,310, Benzo [E] [1,3] Oxazin-4-One Derivatives as Phosphoinositide 3-Kinase Inhibitors, filed Feb. 6, 2012, Patented, U.S. Pat. No. 8,981,087.
U.S. Appl. No. 13/388,164, Tricyclic Heterocyclic Compounds as Phosphoinositide 3-Kinase Inhibitors, filed Mar. 27, 2012, Patented, U.S. Pat. No. 9,200,007.
U.S. Appl. No. 14/920,410, Tricyclic Heterocyclic Compounds as Phosphoinositide 3-Kinase Inhibitors, filed Oct. 22, 2015, Patented, U.S. Pat. No. 9,580,442.
U.S. Appl. No. 15/410,114, Tricyclic Heterocyclic Compounds as Phosphoinositide 3-Kinase Inhibitors, filed Jan. 19, 2017, Patented, U.S. Pat. No. 9,938,290.
U.S. Appl. No. 15/909,011, Tricyclic Heterocyclic Compounds as Phosphoinositide 3-Kinase Inhibitors, filed Mar. 1, 2018, Patented, U.S. Pat. No. 10,501,478.

(Continued)

*Primary Examiner* — Rebecca L Anderson
(74) *Attorney, Agent, or Firm* — DLA Piper LLP (US)

(57) ABSTRACT

A compound of formula I:

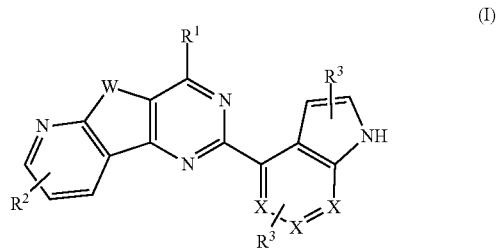

or a pharmaceutically acceptable salt thereof, wherein: W is O, N—H, N—($C_1$-$C_{10}$ alkyl) or S; each X is independently CH or N; $R^1$ is a 5 to 7-membered saturated or unsaturated, optionally substituted heterocycle containing at least 1 heteroatom selected from N or O; $R^2$ is LY; each L is a direct bond, $C_1$-$C_{10}$ alkylene, $C_2$-$C_{10}$ alkenylene or $C_2$-$C_{10}$ alkynylene; Y is an optionally substituted fused, bridged or spirocyclic non-aromatic 5-12 membered heterocycle containing up to 4 heteroatoms selected from N or O; and each $R^3$ is independently H, $C_1$-$C_{10}$ alkyl, halogen, fluoro $C_1$-$C_{10}$ alkyl, O—$C_1$-$C_{10}$ alkyl, NH—$C_1$-$C_{10}$ alkyl, S—$C_1$-$C_{10}$ alkyl, O-fluoro $C_1$-$C_{10}$ alkyl, NH-acyl, NH—C(O)—NH—$C_1$-$C_{10}$ alkyl, C(O)—NH—$C_1$-$C_{10}$ alkyl, aryl or heteroaryl, are useful as inhibitors of the class IA phosphoinositide 3-kinase enzyme, PI3K-p110δ, and therefore have potential utility in the therapy of cancer, immune and inflammatory diseases.

11 Claims, No Drawings

(56) References Cited

U.S. PATENT DOCUMENTS

| | | |
|---|---|---|
| 8,338,592 B2 | 12/2012 | Alexander et al. |
| 8,710,054 B2 | 4/2014 | Alexander et al. |
| 8,921,361 B2 | 12/2014 | Cmiljanovic et al. |
| 8,981,087 B2 | 3/2015 | Shuttleworth et al. |
| 9,200,007 B2 | 12/2015 | Shuttleworth et al. |
| 9,266,879 B2 | 2/2016 | Shuttleworth et al. |
| 9,580,442 B2 | 2/2017 | Shuttleworth et al. |
| 9,663,487 B2 | 5/2017 | Shuttleworth et al. |
| 9,868,749 B2 | 1/2018 | Alexander et al. |
| 9,890,174 B2 | 2/2018 | Alexander et al. |
| 9,932,343 B2 | 4/2018 | Alexander et al. |
| 9,938,290 B2 | 4/2018 | Shuttleworth et al. |
| 9,981,987 B2 | 5/2018 | Shuttleworth et al. |
| 10,035,785 B2 | 7/2018 | Shuttleworth et al. |
| 10,087,179 B2 | 10/2018 | Alexander et al. |
| 10,377,764 B2 | 8/2019 | Shuttleworth et al. |
| 10,442,815 B2 | 10/2019 | Shuttleworth et al. |
| 10,501,478 B2 | 12/2019 | Shuttleworth et al. |
| 10,513,530 B2 | 12/2019 | Shuttleworth et al. |
| 10,668,077 B2 | 6/2020 | Shuttleworth et al. |
| 11,291,669 B2* | 4/2022 | Shuttleworth ....... A61K 31/519 |
| 2002/0151544 A1 | 10/2002 | Hayakawa et al. |
| 2007/0135466 A1 | 6/2007 | Ledeboer et al. |
| 2010/0137302 A1 | 6/2010 | Alexander et al. |
| 2011/0003785 A1 | 1/2011 | Alexander et al. |
| 2011/0201608 A1 | 8/2011 | Hoffmann et al. |
| 2012/0178737 A1 | 7/2012 | Shuttleworth et al. |
| 2013/0079330 A1 | 3/2013 | Alexander et al. |
| 2013/0109688 A1 | 5/2013 | Shuttleworth et al. |
| 2014/0163033 A1 | 6/2014 | Bernal Anchuela et al. |
| 2015/0080395 A1 | 3/2015 | Shuttleworth et al. |
| 2016/0108057 A1 | 4/2016 | Shuttleworth et al. |
| 2016/0113932 A1 | 4/2016 | Stern et al. |
| 2016/0297837 A1 | 10/2016 | Alexander et al. |
| 2016/0304523 A1 | 10/2016 | Alexander et al. |
| 2016/0304530 A1 | 10/2016 | Alexander et al. |
| 2016/0347771 A1 | 12/2016 | Shuttleworth et al. |
| 2016/0376268 A1 | 12/2016 | Alexander et al. |
| 2018/0009826 A1 | 1/2018 | Shuttleworth et al. |
| 2018/0235974 A1 | 8/2018 | Shuttleworth et al. |
| 2018/0243313 A1 | 8/2018 | Shuttleworth et al. |
| 2018/0243317 A1 | 8/2018 | Shuttleworth et al. |
| 2018/0244685 A1 | 8/2018 | Shuttleworth et al. |
| 2018/0244686 A1 | 8/2018 | Shuttleworth et al. |
| 2019/0040079 A1 | 2/2019 | Shuttleworth et al. |
| 2020/0354378 A1 | 11/2020 | Shuttleworth et al. |
| 2021/0275537 A1 | 9/2021 | Shuttleworth et al. |
| 2022/0273667 A1 | 9/2022 | Ward |

FOREIGN PATENT DOCUMENTS

| | | |
|---|---|---|
| GB | 1402431 A | 8/1975 |
| WO | WO-01/83456 A1 | 11/2001 |
| WO | WO-02/02551 A1 | 1/2002 |
| WO | WO-02/085400 A1 | 10/2002 |
| WO | WO-2004/006846 A2 | 1/2004 |
| WO | WO-2004/043956 A1 | 5/2004 |
| WO | 2005117889 A1 | 12/2005 |
| WO | WO-2006/046035 A1 | 5/2006 |
| WO | WO-2006/127587 A1 | 11/2006 |
| WO | WO-2007/084667 A2 | 7/2007 |
| WO | WO-2007/122410 A1 | 11/2007 |
| WO | WO-2007/127183 A1 | 11/2007 |
| WO | WO-2008/064018 A1 | 5/2008 |
| WO | 2008076447 A2 | 6/2008 |
| WO | WO-2008/094992 A2 | 8/2008 |
| WO | WO-2008/121257 A1 | 10/2008 |
| WO | WO-2008/145688 A2 | 12/2008 |
| WO | WO-2008/150827 A1 | 12/2008 |
| WO | WO-2010/015520 A1 | 2/2010 |
| WO | WO-2010/037765 A2 | 4/2010 |
| WO | WO-2010/052569 A2 | 5/2010 |
| WO | WO-2011/012883 A1 | 2/2011 |
| WO | WO-2011/021038 A1 | 2/2011 |
| WO | WO-2011/079231 A1 | 6/2011 |
| WO | WO-2011/135351 A1 | 11/2011 |
| WO | WO-2013/014448 A1 | 1/2013 |
| WO | WO-2013/017480 A1 | 2/2013 |
| WO | WO-2013/132270 A1 | 9/2013 |
| WO | WO-2014/081718 A1 | 5/2014 |
| WO | WO-2014/181137 A1 | 11/2014 |
| WO | WO-2014/210354 A1 | 12/2014 |
| WO | 2015054099 A1 | 4/2015 |
| WO | WO-2015/054355 A1 | 4/2015 |
| WO | WO-2015/121657 A1 | 8/2015 |
| WO | 2016075130 A1 | 5/2016 |
| WO | WO-2017/029514 A1 | 2/2017 |
| WO | WO-2017/029517 A1 | 2/2017 |
| WO | WO-2017/029518 A1 | 2/2017 |
| WO | WO-2017/029519 A1 | 2/2017 |
| WO | WO-2017/029521 A1 | 2/2017 |
| WO | 2021001650 A1 | 1/2021 |

OTHER PUBLICATIONS

U.S. Appl. No. 13/643,210, Naphthridine Derivatives as PI3K Inhibitors for the Treatment of Cancer and Immune-Inflammatory Disease, filed Jan. 7, 2013, Patented, U.S. Pat. No. 9,266,879.

U.S. Appl. No. 14/382,196, Phosphoinositide 3-Kinase Inhibitors, filed Aug. 29, 2014, Patented, U.S. Pat. No. 9,663,487.

U.S. Appl. No. 15/496,511, Phosphoinositide 3-Kinase Inhibitors, filed Apr. 25, 2017, Patented, U.S. Pat. No. 10,035,785.

U.S. Appl. No. 15/117,606, Tricyclic heterocyclic compounds as phosphoinositide 3-kinase inhibitors, filed Aug. 9, 2016, Patented, U.S. Pat. No. 9,981,987.

U.S. Appl. No. 15/961,404, Tricyclic heterocyclic compounds as phosphoinositide 3-kinase inhibitors, filed Apr. 24, 2018, Patented, U.S. Pat. No. 10,513,530.

U.S. Appl. No. 15/753,361, Tricyclic heterocyclic compounds as phosphoinositide 3-kinase inhibitors, filed Feb. 19, 2018, Patented, U.S. Pat. No. 10,377,764.

U.S. Appl. No. 15/753,358, Tricyclic heterocyclic compounds as phosphoinositide 3-kinase inhibitors, filed Feb. 19, 2018, Patented, U.S. Pat. No. 10,442,815.

U.S. Appl. No. 15/753,353, Compositions comprising phosphoinositide 3-kinase inhibitors and a second antiproliferative agent, filed Feb. 19, 2018, Patented, U.S. Pat. No. 10,668,077.

U.S. Appl. No. 16/855,758, Compositions comprising phosphoinositide 3-kinase inhibitors and a second antiproliferative agent, filed Apr. 22, 2020, Published, 2021-0069200.

Alvarez-Rua et al., "Multiple Hydrogen Bonds and Tautomerism in Naphthyridine Derivatives", New J. Chem. 28, 700-07 (2004).

Ameriks et al., "Small Molecule Inhibitors of Phosphoinositide 3-Kinase (PI3K) δ and γ", Current Topics in Medicinal Chemistry, 2009, vol. 9, No. 8, pp. 738-753.

Baldev Singh et al., "Novel cAMP PDE III Inhibitors: 1,6-Naphthyridin-2(18)-ones", Journal of Medicinal Chemistry, American Chemical Society, 35(26): 5858-4865, Jan. 1, 1992, New York.

CAS Registry Nos. 1214438-02-4 and 1214393-37-9 (Mar. 25, 2010).

Cohen et al., Current Opinion in Chemical Biology, 3, 459-465, 1999.

D.A. Kovalskiy et al., "Synthesis of 7-(3-piperidyl)[1,6]naphthyridine and 7-(4-piperidyl)[1,6]naphthyridine", Chemistry of Heterocyclic Compounds, 45(9): 1053-1057, Nov. 24, 2009.

Database Chemcats [Online], Chemical Abstracts Service, Apr. 22, 2011, Columbus, Ohio.

Erik L. Meredith et al., "Identification of Orally Available Naphthyridine Protein Kinase D Inhibitors", Journal of Medicinal Chemistry, 53(15): 5400-5421, Aug. 12, 2010.

Fabbro et al. Pharmacology & Therapeutics 93, 79-98, 2002.

Golub et al., Science, 286, 531-537, 1999.

Hayakawa, et al., "Synthesis and Biological Evaluation of Pyrido[3',2':4,5]furo[3,2-d]pyrimidine Derivatives as Novel PI3 Kinase p110α Inhibitors" Bioorganic & Medicinal Chemistry Letters, 2007, vol. 17, pp. 2438-2442.

(56) References Cited

OTHER PUBLICATIONS

International Preliminary Report on Patentability and Written Opinion of the International Searching Authority for PCT/GB2010/051221 dated Jan. 31, 2012 (7 pages).
International Preliminary Report on Patentability and Written Opinion of the International Searching Authority for PCT/GB2010/051370 dated Feb. 21, 2012 (6 pages).
International Preliminary Report on Patentability and Written Opinion of the International Searching Authority for PCT/GB2011/050824 dated Nov. 6, 2012 (7 pages).
International Preliminary Report on Patentability and Written Opinion of the International Searching Authority for PCT/GB2013/050583 dated Sep. 9, 2014 (6 pages).
International Preliminary Report on Patentability and Written Opinion of the International Searching Authority for PCT/GB2015/050396 dated Aug. 16, 2016 (6 pages).
International Search Report of the International Searching Authority for PCT/GB2010/051221 dated Oct. 7, 2010 (4 pages).
International Search Report of the International Searching Authority for PCT/GB2010/051370 dated Nov. 9, 2010 (4 pages).
International Search Report of the International Searching Authority for PCT/GB2011/050824 dated Jul. 12, 2011 (5 pages).
International Search Report of the International Searching Authority for PCT/GB2013/050583 dated May 6, 2013 (4 pages).
International Search Report of the International Searching Authority for PCT/GB2015/050396 dated Mar. 25, 2015 (3 pages).
Mass, R. D., Int. J. Radiation Oncology Bio. Phys. vol. 58 (3): 932-940, 2004.
Saifuddin, M. et al., "Water-Accelerated Cationic pi-(7-endo) cyclisation: Application to Indole-Based Peri-Annulated Polyheterocycles." European Journal of Organic Chemistry, 2010, 26, 5108-5117.
Somei et al., "Boronation-Thallation, A New Approach to the Synthesis of Indoles Having Aryl and/or a Heteroaryl Substituent at the 4-Position." Chem. Pharm. Bull. 1986, 34, 3971-3.
Verheijen et al., "Phosphatidylinositol 3-kinase (PI3K) inhibitors as anticancer drugs", Drugs of the Future, 2007, vol. 32, No. 6, pp. 537-547.
Hollebecque A et al., (2014), 'A Phase Ib Trial of LY2584702 Tosylate, a p70 S6 Inhibitor, in Combination with Erlotinib or Everolimus in Patients with Solid Tumours,' Eur J Cancer, 50(5):876-84.
Lin L et al., (2014), 'Dual Targeting of Glioblastoma Multiforme with a Proteasome Inhibitor (Velcade) and a Phosphatidylinositol 3-Kinase Inhibitor (ZSTK474),' Int J Oncol, 44(2):557-62.
Notification of the Transmittal of the International Search Report and the Written Opinion of the International Searching Authority, or the Declaration, (form ISA/220), International Application No. PCT/GB2016/052575 , dated Nov. 9, 2016 (13 pages).
Notification of the Transmittal of the International Search Report and the Written Opinion of the International Searching Authority, or the Declaration, (form ISA/220), International Application No. PCT/GB2016/052577 , dated Nov. 9, 2016 (10 pages).
Notification of the Transmittal of the International Search Report and the Written Opinion of the International Searching Authority, or the Declaration, (form ISA/220), International Application No. PCT/GB2016/052578 , dated Oct. 25, 2016 (12 pages).
Notification of the Transmittal of the International Search Report and the Written Opinion of the International Searching Authority, or the Declaration, (form ISA/220), International Application No. PCT/GB2016/052581 , dated Oct. 24, 2016 (13 pages).
Schröder E et al., 'Arzneimittel Chemie Passage,' *Arzneimittelchemie Grundlagen Nerven, Muskeln und Gewebe [Pharmaceutical Chemistry I: Basic, Nerves, Muscles and Tissues]*, (1st. Ed, 1976), Thieme Georg Verla, Stuttgart DE (Publ) pp. 30-33 and Table 8 XP002186820.
Tao J et al., (2013), 'Combined Treatment of BTK and PI3K Inhibitors Synergistically Disrupts BCR-Signaling, Overcomes Microenvironment-Mediated Survival and Drug Resistance in Mantle Cell Lymphoma,' Proceedings of the 104th Annual Meeting of the American Association for Cancer Research, Apr. 6-10, 2013, Washington, D.C. Philadelphia PA, AACR Abstract #4944, OASIS, Chicago, IL (Publ) (2 pages) [retrieved on Jul. 16, 2014 at <http://wwwabstractsonline.com/Plan/ViewAbstract.aspx?Key=605> . . . ] (ABSTRACT).
Yamada T et al., (2013) 'A Novel HDAC Inhibitor OBP-801 and a PI3K Inhibitor LY294002 Synergistically Induce Apoptosis via the Suppression of Survivin and XIAP in Renal Cell Carcinoma,' Int J Oncol, 43(4):1080-6.
Zhong H et al., (2013) 'Synergistic Effects of Concurrent Blockade of PI3K and MEK Pathways in Pancreatic Cancer Preclinical Models,' PLoS One, 8(10):e77243.
Zhou W et al., (2009) Novel Mutant-Selective EGFR Kinase Inhibitors Against EGFR T790M, Nature, 462(7276):1070-4 [NIH Public Access Version].
Annex to Form PCT/ISA/206 Communication relating to the results of the partial international search for International Application No. PCT/GB2016/052571 dated Nov. 9, 2016 (4 pages).
Written Opinion of the International Searching Authority for PCT/GB2016/052571 dated Feb. 23, 2017 (9 pages).
International Search Report of the International Searching Authority for PCT/GB2016/052571 dated Feb. 23, 2017 (6 pages).
Brachmann, S. et al. PI3K and mTOR inhibitors—a new generation of targeted anticancer agents. Current Opinion in Cell Biology. 2009, 21, 194-198.
Liu, Q. et al. mTOR mediated anti-cancer drug discovery. Drug Discovery Today: Therapeutic Strategies. 2009, 6 (2), 47-55.
Shuttleworth, S. J. et al. Progress in the Preclinical Discovery and Clinical Development of Class I and Dual Class I/IV Phosphoinositide 3-Kinase (PI3K) Inhibitors. Current Medicinal Chemistry, 2011, 18, 2686-2714.
Zhao, X. et al. Discovery of novel Bruton's tyrosine kinase (BTK) inhibitors bearing a pyrrolo[2,3-d]pyrimidine scaffold. Bioorganic and Medicinal Chemistry, 23, 2015, 891-901.
Bianchi et al., "Team work matters: dual inhibition puts non-Hodgkin lymphoma under siege", Clin. Cancer Res., 2014, 20(18):5863-5865.
Bodo et al., "The PI3K inhibitor GS-1101 (CAL-101) synergistically potentiates HDAC-induced proliferation inhibition and apoptosis through the activation of JNK in lymphoma cells", Blood, 2012, 120(21):3714.
European Search Report for EP 18202398.6 dated Feb. 15, 2019.
International Search Report and Written Opinion for PCT/GB2020/051582 dated Oct. 8, 2020.

* cited by examiner

TRICYCLIC HETEROCYCLIC COMPOUNDS AS PHOSPHOINOSITIDE 3-KINASE INHIBITORS

CROSS-REFERENCE TO RELATED APPLICATIONS

This application is a continuation of U.S. patent application Ser. No. 16/678,565, filed Nov. 8, 2019, which is a continuation of U.S. patent application Ser. No. 15/961,404, filed Apr. 24, 2018 (now U.S. Pat. No. 10,513,530), which is a continuation of U.S. patent application Ser. No. 15/117,606, filed Aug. 9, 2016 (now U.S. Pat. No. 9,981,987); which is a national stage filing under 35 U.S.C. § 371 of PCT/GB2015/050396, filed Feb. 12, 2015, which claims priority to Patent Application No. GB1402431.9, filed Feb. 12, 2014, the entire disclosure of each of which is incorporated by reference herein.

FIELD OF THE INVENTION

The present invention relates to novel compounds which act as inhibitors of the class IA phosphoinositide 3-kinase enzyme, PI3K-p110δ, for the treatment of cancer, immune and inflammatory diseases.

BACKGROUND OF THE INVENTION

The phosphoinositide 3-kinases (PI3Ks) constitute a family of lipid kinases involved in the regulation of a network of signal transduction pathways that control a range of cellular processes. PI3Ks are classified into three distinct subfamilies, named class I, II, and III based upon their substrate specificities. Class IA PI3Ks possess a p110α, p110β, or p110δ catalytic subunit complexed with one of three regulatory subunits, p85α, p85β or p55δ. Class IA PI3Ks are activated by receptor tyrosine kinases, antigen receptors, G-protein coupled receptors (GPCRs), and cytokine receptors. The class IA PI3Ks primarily generate phosphatidylinositol-3,4,5-triphosphate (PI(3,4,5)P$_3$), a second messenger that activates the downstream target AKT. The consequences of biological activation of AKT include tumour cell progression, proliferation, survival and growth, and there is significant evidence suggesting that the PI3K/AKT pathway is dysregulated in many human cancers. Additionally, PI3K activity has been implicated in endocrinology, cardiovascular disease, immune disorders and inflammation. It has been established that PI3K-p110δ plays a critical role in the recruitment and activation of immune and inflammatory cells. PI3K-p110δ is also upregulated in a number of human tumours and plays a key role in tumour cell proliferation and survival.

Compounds which are able to modulate p110δ activity have important therapeutic potential in cancer and immune and inflammatory disorders.

WO 2011/021038 describes compounds which act as inhibitors of PI3K-p110δ.

SUMMARY OF THE INVENTION

The present invention relates to a selection of compounds having increased activity and/or bioavailability over the compounds described in WO 2011/021038. Without wishing to be bound by theory, this is believed to be owing to the provision of a bridged or spirocyclic non-aromatic group in the R$^2$ position.

Therefore, the present invention is a compound of Formula I:

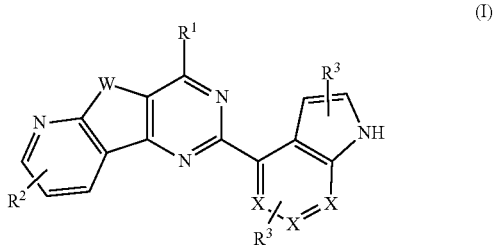

(I)

or a pharmaceutically acceptable salt thereof, wherein:

W is O, N—H, N—(C$_1$-C$_{10}$ alkyl) or S;

each X is selected independently for each occurrence from CH, CR$^3$, or N;

R$^1$ is a 5 to 7-membered saturated or unsaturated, optionally substituted heterocycle containing at least 1 heteroatom selected from N or O;

R$^2$ is L-Y;

each L is selected from the group consisting of a direct bond, C$_1$-C$_{10}$ alkylene, C$_2$-C$_{10}$ alkenylene and C$_2$-C$_{10}$ alkynylene;

Y is an optionally substituted fused, bridged or spirocyclic non-aromatic heterocycle containing up to 4 heteroatoms (for example, one, two, three or four heteroatoms) each independently selected from N or O, and comprising 5 to 12 carbon or heteroatoms in total; and each R$^3$ is independently H, C$_1$-C$_{10}$ alkyl, halogen, fluoro C$_1$-C$_{10}$ alkyl, O—C$_1$-C$_{10}$ alkyl, —NH—C$_1$-C$_{10}$ alkyl, S—C$_1$-C$_{10}$ alkyl, O-fluoro C$_1$-C$_{10}$ alkyl, NH-acyl, NH—C(O)—NH—C$_1$-C$_{10}$ alkyl, C(O)—NH—C$_1$-C$_{10}$ alkyl, aryl or heteroaryl.

DESCRIPTION OF THE PREFERRED EMBODIMENTS

Definitions

As used herein, "alkyl" means a C$_1$-C$_{10}$ alkyl group, which can be linear or branched. Preferably, it is a C$_1$-C$_6$ alkyl moiety. More preferably, it is a C$_1$-C$_4$ alkyl moiety. Examples include methyl, ethyl, n-propyl and t-butyl. It may be divalent, e.g. propylene.

As used herein, "alkenyl" means a C$_2$-C$_{10}$ alkenyl group. Preferably, it is a C$_2$-C$_6$ alkenyl group. More preferably, it is a C$_2$-C$_4$ alkenyl group. The alkenyl radicals may be mono- or di-saturated, more preferably monosaturated. Examples include vinyl, allyl, 1-propenyl, isopropenyl and 1-butenyl. It may be divalent, e.g. propenylene.

As used herein, "alkynyl" is a C$_2$-C$_{10}$ alkynyl group which can be linear or branched. Preferably, it is a C$_2$-C$_4$ alkynyl group or moiety. It may be divalent.

Each of the C$_1$-C$_{10}$ alkyl, C$_2$-C$_{10}$ alkenyl and C$_1$-C$_{10}$ alkynyl groups may be optionally substituted with each other, i.e. C$_1$-C$_{10}$ alkyl optionally substituted with C$_2$-C$_{10}$ alkenyl. They may also be optionally substituted with aryl, cycloalkyl (preferably C$_3$-C$_{10}$), aryl or heteroaryl. They may also be substituted with halogen (e.g. F, Cl), NH$_2$, NO$_2$ or hydroxyl. Preferably, they may be substituted with up to 10 halogen atoms or more preferably up to 5 halogens. For example, they may be substituted by 1, 2, 3, 4 or 5 halogen atoms. Preferably, the halogen is fluorine. For example, they may be substituted with CF$_3$, CHF$_2$, CH$_2$CF$_3$, CH$_2$CHF$_2$ or CF$_2$CF$_3$.

As used herein, the term "fluoro $C_1$-$C_{10}$ alkyl" means a $C_1$-$C_{10}$ alkyl substituted with one or more fluorine atoms. Preferably, one, two, three, four or five fluorine atoms. Examples of "fluoro $C_1$-$C_{10}$ alkyl" are $CF_3$, $CHF_2$, $CH_2F$, $CH_2CF_3$, $CH_2CHF_2$ or $CF_2CF_3$.

As used herein, "aryl" means a monocyclic, bicyclic, or tricyclic monovalent or divalent (as appropriate) aromatic radical, such as phenyl, biphenyl, naphthyl, anthracenyl, which can be optionally substituted with up to five substituents preferably selected from the group of $C_1$-$C_6$ alkyl, hydroxy, $C_1$-$C_3$ hydroxyalkyl, $C_1$-$C_3$ alkoxy, $C_1$-$C_3$ haloalkoxy, amino, $C_1$-$C_3$ mono alkylamino, $C_1$-$C_3$ bis alkylamino, $C_1$-$C_3$ acylamino, $C_1$-$C_3$ aminoalkyl, mono ($C_1$-$C_3$ alkyl) amino $C_1$-$C_3$ alkyl, bis($C_1$-$C_3$ alkyl) amino $C_1$-$C_3$ alkyl, $C_1$-$C_3$-acylamino, $C_1$-$C_3$ alkyl sulfonylamino, halo, nitro, cyano, trifluoromethyl, carboxy, $C_1$-$C_3$ alkoxycarbonyl, aminocarbonyl, mono $C_1$-$C_3$ alkyl aminocarbonyl, bis $C_1$-$C_3$ alkyl aminocarbonyl, —$SO_3H$, $C_1$-$C_3$ alkylsulfonyl, aminosulfonyl, mono $C_1$-$C_3$ alkyl aminosulfonyl and bis $C_1$-$C_3$-alkyl aminosulfonyl.

As used herein, "heteroaryl" means a monocyclic, bicyclic or tricyclic monovalent or divalent (as appropriate) aromatic radical containing up to four heteroatoms selected from oxygen, nitrogen and sulfur, such as thiazolyl, isothiazolyl, tetrazolyl, imidazolyl, oxazolyl, isoxazolyl, thienyl, pyrazolyl, pyridinyl, pyrazinyl, pyrimidinyl, indolyl, quinolyl, isoquinolyl, triazolyl, thiadiazolyl, oxadiazolyl, said radical being optionally substituted with up to three substituents preferably selected from the group of $C_1$-$C_6$ alkyl, hydroxy, $C_1$-$C_3$ hydroxyalkyl, $C_1$-$C_3$ alkoxy, $C_1$-$C_3$ haloalkoxy, amino, $C_1$-$C_3$ mono alkylamino, $C_1$-$C_3$ bis alkylamino, $C_1$-$C_3$ acylamino, $C_1$-$C_3$ aminoalkyl, mono ($C_1$-$C_3$ alkyl) amino $C_1$-$C_3$ alkyl, bis ($C_1$-$C_3$ alkyl) amino $C_1$-$C_3$ alkyl, $C_1$-$C_3$-acylamino, $C_1$-$C_3$ alkyl sulfonylamino, halo, nitro, cyano, trifluoromethyl, carboxy, $C_1$-$C_3$ alkoxycarbonyl, aminocarbonyl, mono $C_1$-$C_3$ alkyl aminocarbonyl, bis $C_1$-$C_3$ alkyl aminocarbonyl, —$SO_3H$, $C_1$-$C_3$ alkylsulfonyl, aminosulfonyl, mono $C_1$-$C_3$ alkyl aminosulfonyl and bis $C_1$-$C_3$-alkyl aminosulfonyl.

As used herein, the term "heterocycle" or "heterocycoalkyl" is a mono- or di-valent carbocyclic radical containing up to 4 heteroatoms selected from oxygen, nitrogen and sulfur. Preferably, it contains one or two heteroatoms. Preferably, at least one of the heteroatoms is nitrogen. It may be monocyclic or bicyclic. It is preferably saturated. Examples of heterocycles are piperidine, piperazine, thiomorpholine, morpholine, azetidine or oxetane. More preferably, the heterocycle is morpholine.

The heterocyclic ring may be mono- or di-unsaturated. The radical may be optionally substituted with up to three substituents independently selected from $C_1$-$C_6$ alkyl, hydroxy, $C_1$-$C_3$ hydroxyalkyl, $C_1$-$C_3$ alkoxy, $C_1$-$C_3$ haloalkoxy, amino, $C_1$-$C_3$ mono alkylamino, $C_1$-$C_3$ bis alkylamino, $C_1$-$C_3$ acylamino, $C_1$-$C_3$ aminoalkyl, mono ($C_1$-$C_3$ alkyl) amino $C_1$-$C_3$ alkyl, bis ($C_1$-$C_3$ alkyl) amino $C_1$-$C_3$ alkyl, $C_1$-$C_3$-acylamino, $C_1$-$C_3$ alkyl sulfonylamino, halo (e.g. F), nitro, cyano, carboxy, $C_1$-$C_3$-haloalkyl (e.g. $CF_3$), $C_1$-$C_3$ alkoxycarbonyl, aminocarbonyl, mono $C_1$-$C_3$ alkyl aminocarbonyl, bis $C_1$-$C_3$ alkyl aminocarbonyl, —$SO_3H$, $C_1$-$C_3$ alkylsulfonyl, aminosulfonyl, mono $C_1$-$C_3$ alkyl aminosulfonyl and bis $C_1$-$C_3$-alkyl aminosulfonyl.

In summary, each of the groups defined above, i.e., alkyl, alkenyl, alkynyl, aryl, heteroaryl, heterocycle, heterocycloalkyl, may be optionally substituted with up to three substituents preferably selected from the group of $C_1$-$C_6$ alkyl, hydroxy, $C_1$-$C_3$ hydroxyalkyl, $C_1$-$C_3$ alkoxy, $C_1$-$C_3$ haloalkoxy, amino, $C_1$-$C_3$ mono alkylamino, $C_1$-$C_3$ bis alkylamino, $C_1$-$C_3$ acylamino, $C_1$-$C_3$ aminoalkyl, mono ($C_1$-$C_3$ alkyl) amino $C_1$-$C_3$ alkyl, bis ($C_1$-$C_3$ alkyl) amino $C_1$-$C_3$ alkyl, $C_1$-$C_3$-acylamino, $C_1$-$C_3$ alkyl sulfonylamino, acyl, halo (e.g. fluoro), nitro, cyano, trifluoromethyl, carboxy, $C_1$-$C_3$ alkoxycarbonyl, aminocarbonyl, mono $C_1$-$C_3$ alkyl aminocarbonyl, bis $C_1$-$C_3$ alkyl aminocarbonyl, —$SO_3H$, $C_1$-$C_3$ alkylsulfonyl, aminosulfonyl, mono $C_1$-$C_3$ alkyl aminosulfonyl and bis $C_1$-$C_3$-alkyl aminosulfonyl.

It should be noted that —NH—$C_1$-$C_{10}$ alkyl, NH-acyl, NH—C(O)—NH—$C_1$-$C_{10}$ alkyl and C(O)—NH—$C_1$-$C_{10}$ alkyl can also be written as —N—$C_1$-$C_{10}$ alkyl, N-acyl, N—C(O)—N—$C_1$-$C_{10}$ alkyl and C(O)—N—$C_1$-$C_{10}$ alkyl.

As used herein, the above groups can be followed by the suffix -ene. This means that the group is divalent, i.e. a linker group.

As used herein, the term "fused" is intended to take its usual meaning within the art of organic chemistry. Fused systems, for example fused bicyclic systems, are those in which two rings share two and only two atoms.

As used herein, the term "bridged" is intended to take its usual meaning within the art of organic chemistry. Bridged compounds are compounds which contain interlocking rings. According to the invention, the atoms of the bridged non-aromatic group which form the bridgehead is either a tertiary carbon atom (when the remaining atom is hydrogen) or a quaternary carbon atom (when the remaining atom is not hydrogen). The bridge can be considered to be a chain of atoms (for example, alkyl) or a single atom (for example, O, S, N, C) connecting two bridgeheads.

As used herein, the term "spirocyclic" is intended to take its usual meaning within the art of organic chemistry. For example, a spirocyclic compound is a bicycle whose rings are attached though just one atom (known as a spiroatom). The rings may be different in size, or they may be the same size. Preferably, according to the invention, the two rings which are joined via the same atom are non-aromatic heterocycles, preferably heterocycloalkyls. For example, the spirocyclic non-aromatic group of Formula I may be a bicycle wherein both rings are heterocycloalkyl and are attached through the same atom, preferably a carbon atom.

Compounds with which the invention is concerned which may exist in one or more stereoisomeric form, because of the presence of asymmetric atoms or rotational restrictions, can exist as a number of stereoisomers with R or S stereochemistry at each chiral centre or as atropisomeres with R or S stereochemistry at each chiral axis. The invention includes all such enantiomers and diastereoisomers and mixtures thereof.

Preferred Groups of the Invention

Preferably, a compound of the invention is as defined in claim 1, but may additionally be a compound where at least one $R^3$ is $NH_2$.

Preferably, $R^1$ is represented by any of the following structures:

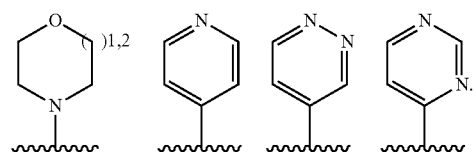

Most preferably, $R^1$ is morpholine.

In a preferred embodiment of the invention, W is oxygen or sulphur, preferably oxygen.

Preferably X is CH.

Preferably $R^3$ is H, $C_1$-$C_{10}$ alkyl, halogen or fluoro $C_1$-$C_{10}$ alkyl. More preferably $R^3$ is H.

Preferably, the 6,5-ring system in Formula I is an indole. In other words, $R^3$ is hydrogen and X is CH.

$R^2$ may be attached to any suitable atom on the aryl group, as depicted in general formula I. However, it is preferred that $R^2$ is attached to the meta-position of the pyridine ring. For example, if the nitrogen atom of the pyridine is labelled as atom number 1, then $R^2$ is attached in the 3-position.

$R^2$ is LY. Preferably, L is $C_1$-$C_{10}$ alkylene, preferably methylene.

Preferably, Y is a an optionally substituted bridged or spirocyclic heterocycloalkyl group containing up to 4 heteroatoms selected from N or O, and comprising 5 to 12 atoms in total.

Preferably, Y contains one or two heteroatoms, preferably two heteroatoms. More preferably, at least one of the heteroatoms is nitrogen and Y is bonded to L through the nitrogen atom, as depicted in the preferable Y groups below:

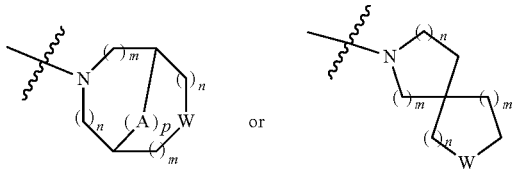

wherein:
A is selected from the group consisting of O, S, $NR^4$, optionally substituted $C_1$-$C_3$ alkylene, $C_2$-$C_3$ alkenylene and $C_2$-$C_3$ alkynylene;
W is selected from the group consisting of $NR^4$, O and $CH_2$;
wherein $R^4$ is selected from the group consisting of H, optionally substituted $C_1$-$C_{10}$ alkyl, $C_1$-$C_{10}$ alkenyl, $C_1$-$C_{10}$ alkynyl and $C_1$-$C_3$ halofluoroalkyl;
p is selected from 0, 1 or 2;
each m is independently selected from 0, 1 or 2; and
each n is independently selected from 1, 2 or 3.

Preferably, A is O or $C_1$-$C_3$ alkylene, most preferably methylene.

Preferably, W is O or $CH_2$, most preferably O.

When $R^4$ is present, it is preferably H, $C_1$-$C_3$ alkyl or $C_1$-$C_3$ halofluoroalkyl. More preferably, $R^4$ is H.

Preferably, each m and n is selected so as to form 5-, 6- or 7-membered nitrogen containing heterocycloalkyl groups. Preferably, p is 1. In particular, when A is O, S or $NR^4$, p is 1.

Y is preferably bicyclic, more preferably bridged bicyclic or spirocyclic bicyclic.

Even more preferably, Y is selected from one of the following groups:

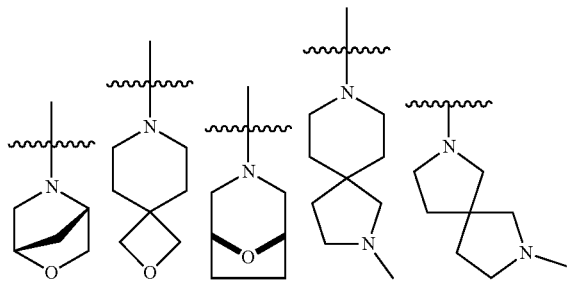

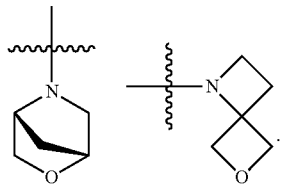

In certain embodiments, provided herein are compounds represented by:

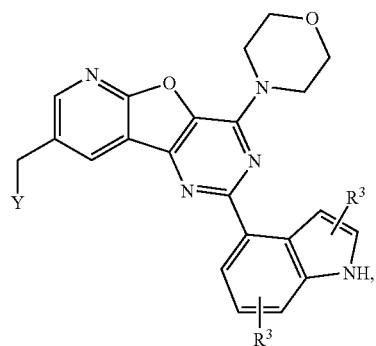

where Y and $R^3$ are defined above.

In another embodiment, provided herein are compounds represented by:

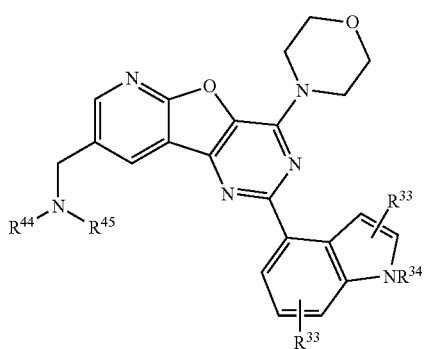

and pharmaceutically acceptable salts thereof, wherein:
$R_{33}$ is independently selected for each occurrence from the group consisting of H, halogen, NH—$C_{1-3}$alkyl, $NH_2$, $C_{1-6}$alkyl and —O—$C_{1-6}$alkyl (wherein $C_{1-6}$alkyl for each occurrence is optionally substituted by one, two or three substituents selected from halogen and hydroxyl);
$R^{34}$ is selected from H or $C_{1-3}$alkyl;
$R^{44}$ and $R^{45}$, when taken together with the nitrogen to which they are attached form a 7-10 membered bicyclic spirocycle or bridged heterocycle each having an additional heteroatom selected from O, S, or $NR^{55}$, wherein $R^{55}$ is H or $C_{1-3}$alkyl.

For example, $R^{44}$ and $R^{45}$, when taken together with the nitrogen to which they are attached may form a 7-8 membered bicyclic bridged heterocycle represented by:

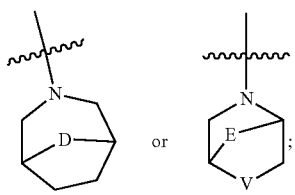

wherein D is O, S or NR$^{55}$; E is O or (CH$_2$)$_r$, wherein r is 1 or 2, and V is O or NR$^{55}$, wherein R$^{55}$ is H or C$_{1-3}$alkyl.

In another exemplary embodiment, R$^{44}$ and R$^{45}$, when taken together with the nitrogen to which they are attached form a 7-10 membered spirocycle having one additional heteroatom selected from O or NR$^{55}$, wherein R$^{55}$ is H or C$_{1-3}$alkyl. Alternatively, R$^{44}$ and R$^{45}$, taken together with the nitrogen to which they are attached may be a Y substituent as described above.

Examples of structures embodying the invention are:

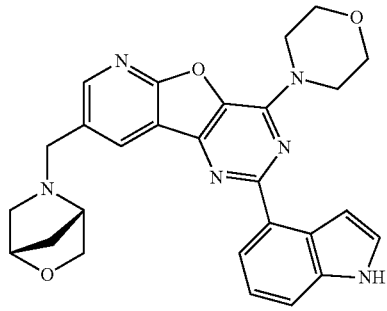

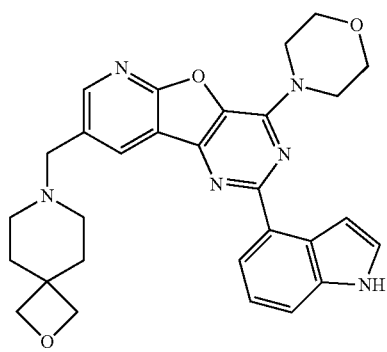

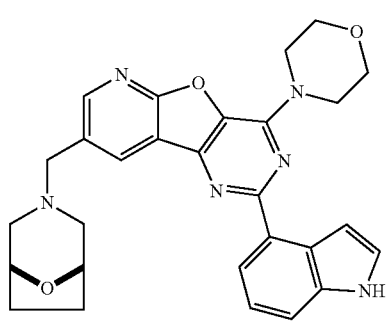

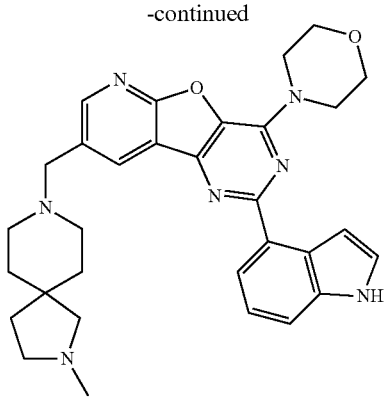

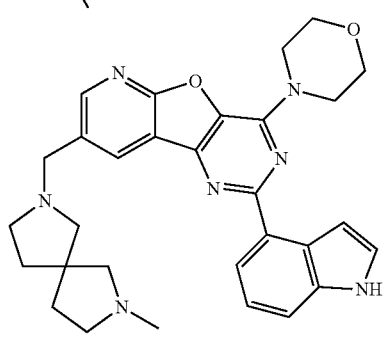

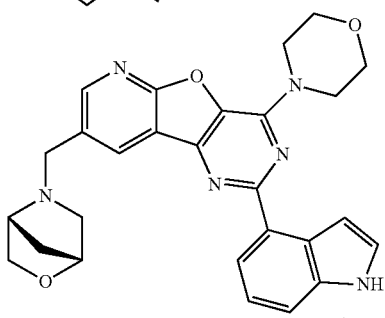

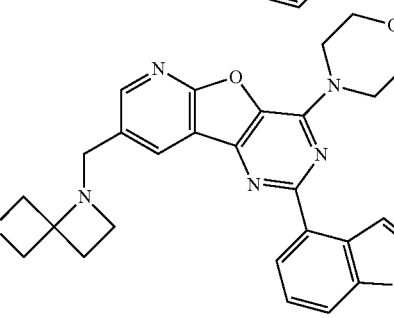

A pharmaceutical composition of the invention typically contains up to 85 wt % of a compound of the invention. More typically, it contains up to 50 wt % of a compound of the invention. Preferred pharmaceutical compositions are sterile and pyrogen-free. Further, the pharmaceutical compositions provided by the invention typically contain a compound of the invention which is a substantially pure optical isomer. Preferably, the pharmaceutical composition comprises a pharmaceutically acceptable salt form of a compound of the invention. For example, contemplated herein is a pharmaceutically acceptable composition comprising a disclosed compound and a pharmaceutically acceptable excipient.

As used herein, a pharmaceutically acceptable salt is a salt with a pharmaceutically acceptable acid or base. Pharmaceutically acceptable acids include both inorganic acids such as hydrochloric, sulphuric, phosphoric, diphosphoric, hydrobromic or nitric acid and organic acids such as citric, fumaric, maleic, malic, ascorbic, succinic, tartaric, benzoic, acetic, methanesulphonic, ethanesulphonic, salicylic, stearic, benzenesulphonic or p-toluenesulphonic acid. Pharmaceutically acceptable bases include alkali metal (e.g. sodium or potassium) and alkali earth metal (e.g. calcium or magnesium) hydroxides and organic bases such as alkyl amines, aryl amines or heterocyclic amines.

For the avoidance of doubt, the present invention also embraces prodrugs which react in vivo to give a compound of the present invention.

The compounds of the invention may be prepared by synthetic routes that will be apparent to those skilled in the art, e.g. based on the Examples.

The compounds of the invention and compositions comprising them may be administered in a variety of dosage forms. In one embodiment, a pharmaceutical composition comprising a compound of the invention may be formulated in a format suitable for oral, rectal, parenteral, intranasal or transdermal administration or administration by inhalation or by suppository. Typical routes of administration are parenteral, intranasal or transdermal administration or administration by inhalation.

The compounds of the invention can be administered orally, for example as tablets, troches, lozenges, aqueous or oily suspensions, dispersible powders or granules. Preferred pharmaceutical compositions of the invention are compositions suitable for oral administration, for example tablets and capsules. In some embodiments, disclosed compounds may have significantly higher oral bioavailability as compared to compounds having a non-spirocycle or non-bridged heterocyclic moiety, e.g., at $R^2$ above.

The compounds of the invention may also be administered parenterally, whether subcutaneously, intravenously, intramuscularly, intrasternally, transdermally or by infusion techniques. The compounds may also be administered as suppositories.

The compounds of the invention may also be administered by inhalation. An advantage of inhaled medications is their direct delivery to the area of rich blood supply in comparison to many medications taken by oral route. Thus, the absorption is very rapid as the alveoli have an enormous surface area and rich blood supply and first pass metabolism is bypassed. A further advantage may be to treat diseases of the pulmonary system, such that delivering drugs by inhalation delivers them to the proximity of the cells which are required to be treated.

The present invention also provides an inhalation device containing such a pharmaceutical composition. Typically said device is a metered dose inhaler (MDI), which contains a pharmaceutically acceptable chemical propellant to push the medication out of the inhaler.

The compounds of the invention may also be administered by intranasal administration. The nasal cavity's highly permeable tissue is very receptive to medication and absorbs it quickly and efficiently, more so than drugs in tablet form. Nasal drug delivery is less painful and invasive than injections, generating less anxiety among patients. By this method absorption is very rapid and first pass metabolism is usually bypassed, thus reducing inter-patient variability. Further, the present invention also provides an intranasal device containing such a pharmaceutical composition.

The compounds of the invention may also be administered by transdermal administration. The present invention therefore also provides a transdermal patch containing a compound of the invention.

The compounds of the invention may also be administered by sublingual administration. The present invention therefore also provides a sub-lingual tablet comprising a compound of the invention.

A compound of the invention may also be formulated with an agent which reduces degradation of the substance by processes other than the normal metabolism of the patient, such as anti-bacterial agents, or inhibitors of protease enzymes which might be the present in the patient or in commensural or parasite organisms living on or within the patient, and which are capable of degrading the compound.

Liquid dispersions for oral administration may be syrups, emulsions and suspensions.

Suspensions and emulsions may contain as carrier, for example a natural gum, agar, sodium alginate, pectin, methylcellulose, carboxymethylcellulose, or polyvinyl alcohol. The suspension or solutions for intramuscular injections may contain, together with the active compound, a pharmaceutically acceptable carrier, e.g. sterile water, olive oil, ethyl oleate, glycols, e.g. propylene glycol, and if desired, a suitable amount of lidocaine hydrochloride.

Solutions for injection or infusion may contain as carrier, for example, sterile water or preferably they may be in the form of sterile, aqueous, isotonic saline solutions.

The compounds of the present invention can be used in both the treatment and prevention of cancer and can be used in a monotherapy or in a combination therapy. When used in a combination therapy, the compounds of the present invention are typically used together with small chemical compounds such as platinum complexes, anti-metabolites, DNA topoisomerase inhibitors, radiation, antibody-based therapies (for example herceptin and rituximab), anti-cancer vaccination, gene therapy, cellular therapies, hormone therapies or cytokine therapy.

In one embodiment of the invention a compound of the invention is used in combination with another chemotherapeutic or antineoplastic agent in the treatment of a cancer. Examples of such other chemotherapeutic or antineoplastic agents include platinum complexes including cisplatin and carboplatin, mitoxantrone, vinca alkaloids for example vincristine and vinblastine, anthracycline antibiotics for example daunorubicin and doxorubicin, alkylating agents for example chlorambucil and melphalan, taxanes for example paclitaxel, antifolates for example methotrexate and tomudex, epipodophyllotoxins for example etoposide, camptothecins for example irinotecan and its active metabolite SN38 and DNA methylation inhibitors for example the DNA methylation inhibitors disclosed in WO02/085400.

According to the invention, therefore, products are provided which contain a compound of the invention and another chemotherapeutic or antineoplastic agent as a combined preparation for simultaneous, separate or sequential use in alleviating a cancer. Also provided according to the invention is the use of compound of the invention in the manufacture of a medicament for use in the alleviation of cancer by coadministration with another chemotherapeutic or antineoplastic agent. The compound of the invention and the said other agent may be administrated in any order. In both these cases the compound of the invention and the other agent may be administered together or, if separately, in any order as determined by a physician.

The PI3K inhibitors of the present invention may also be used to treat abnormal cell proliferation due to insults to body tissue during surgery in a human patient. These insults may arise as a result of a variety of surgical procedures such as joint surgery, bowel surgery, and cheloid scarring. Diseases that produce fibrotic tissue that may be treated using the PI3K inhibitors of the present invention include emphysema. Repetitive motion disorders that may be treated using the present invention include carpal tunnel syndrome. An example of a cell proliferative disorder that may be treated using the invention is a bone tumour.

Proliferative responses associated with organ transplantation that may be treated using PI3K inhibitors of the invention include proliferative responses contributing to potential organ rejections or associated complications. Specifically, these proliferative responses may occur during transplantation of the heart, lung, liver, kidney, and other body organs or organ systems.

Abnormal angiogenesis that may be treated using this invention include those abnormal angiogenesis accompanying rheumatoid arthritis, ischemic-reperfusion related brain edema and injury, cortical ischemia, ovarian hyperplasia and hypervascularity, polycystic ovary syndrome, endometriosis, psoriasis, diabetic retinopathy, and other ocular angiogenic diseases such as retinopathy of prematurity (retrolental fibroplastic), macular degeneration, corneal graft rejection, neuroscular glaucoma and Oster Webber syndrome.

Examples of diseases associated with uncontrolled angiogenesis that may be treated according to the present invention include, but are not limited to retinal/choroidal neovascularisation and corneal neovascularisation. Examples of diseases which include some component of retinal/choroidal neovascularisation include, but are not limited to, Best's diseases, myopia, optic pits, Stargart's diseases, Paget's disease, vein occlusion, artery occlusion, sickle cell anaemia, sarcoid, syphilis, pseudoxanthoma elasticum carotid apo structive diseases, chronic uveitis/vitritis, mycobacterial infections, Lyme's disease, systemic lupus erythematosus, retinopathy of prematurity, Eale's disease, diabetic retinopathy, macular degeneration, Bechet's diseases, infections causing a retinitis or chroiditis, presumed ocular histoplasmosis, pars planitis, chronic retinal detachment, hyperviscosity syndromes, toxoplasmosis, trauma and post-laser complications, diseases associated with rubesis (neovascularisation of the angle) and diseases caused by the abnormal proliferation of fibrovascular or fibrous tissue including all forms of proliferative vitreoretinopathy. Examples of corneal neovascularisation include, but are not limited to, epidemic keratoconjunctivitis, Vitamin A deficiency, contact lens overwear, atopic keratitis, superior limbic keratitis, pterygium keratitis sicca, sjogrens, acne rosacea, phylectenulosis, diabetic retinopathy, retinopathy of prematurity, corneal graft rejection, Mooren ulcer, Terrien's marginal degeneration, marginal keratolysis, polyarteritis, Wegener sarcoidosis, Scleritis, periphigoid radial keratotomy, neovascular glaucoma and retrolental fibroplasia, syphilis, Mycobacteria infections, lipid degeneration, chemical burns, bacterial ulcers, fungal ulcers, Herpes simplex infections, Herpes zoster infections, protozoan infections and Kaposi sarcoma.

Chronic inflammatory diseases associated with uncontrolled angiogenesis may also be treated using PI3K inhibitors of the present invention. Chronic inflammation depends on continuous formation of capillary sprouts to maintain an influx of inflammatory cells. The influx and presence of the inflammatory cells produce granulomas and thus maintains the chronic inflammatory state. Inhibition of angiogenesis using a PI3K inhibitor alone or in conjunction with other anti-inflammatory agents may prevent the formation of the granulosmas and thus alleviate the disease. Examples of chronic inflammatory diseases include, but are not limited to, inflammatory bowel diseases such as Crohn's disease and ulcerative colitis, psoriasis, sarcoidosis, and rheumatoid arthritis.

Inflammatory bowel diseases such as Crohn's disease and ulcerative colitis are characterised by chronic inflammation and angiogenesis at various sites in the gastrointestinal tract. For example, Crohn's disease occurs as a chronic transmural inflammatory disease that most commonly affects the distal ileum and colon but may also occur in any part of the gastrointestinal tract from the mouth to the anus and perianal area. Patients with Crohn's disease generally have chronic diarrhoea associated with abdominal pain, fever, anorexia, weight loss and abdominal swelling. Ulcerative colitis is also a chronic, nonspecific, inflammatory and ulcerative disease arising in the colonic mucosa and is characterised by the presence of bloody diarrhoea. These inflammatory bowel diseases are generally caused by chronic granulomatous inflammation throughout the gastrointestinal tract, involving new capillary sprouts surrounded by a cylinder of inflammatory cells. Inhibition of angiogenesis by these inhibitors should inhibit the formation of the sprouts and prevent the formation of granulomas. Inflammatory bowel diseases also exhibit extra intestinal manifestations, such as skin lesions. Such lesions are characterized by inflammation and angiogenesis and can occur at many sites other the gastrointestinal tract. Inhibition of angiogenesis by PI3K inhibitors according to the present invention can reduce the influx of inflammatory cells and prevent lesion formation.

Sarcoidosis, another chronic inflammatory disease, is characterized as a multisystem granulomatous disorder. The granulomas of this disease can form anywhere in the body. Thus, the symptoms depend on the site of the granulomas and whether the disease is active. The granulomas are created by the angiogenic capillary sprouts providing a constant supply of inflammatory cells. By using PI3K inhibitors according to the present invention to inhibit angiogenesis, such granulomas formation can be inhibited. Psoriasis, also a chronic and recurrent inflammatory disease, is characterised by papules and plaques of various sizes. Treatment using these inhibitors alone or in conjunction with other anti-inflammatory agents should prevent the formation of new blood vessels necessary to maintain the characteristic lesions and provide the patient relief from the symptoms.

Rheumatoid arthritis (RA) is also a chronic inflammatory disease characterised by non-specific inflammation of the peripheral joints. It is believed that the blood vessels in the synovial lining of the joints undergo angiogenesis. In addition to forming new vascular networks, the endothelial cells release factors and reactive oxygen species that lead to pannus growth and cartilage destruction. The factors involved in angiogenesis may actively contribute to, and help maintain, the chronically inflamed state of rheumatoid arthritis. Treatment using PI3K inhibitors according to the present invention alone or in conjunction with other anti-RA agents may prevent the formation of new blood vessels necessary to maintain the chronic inflammation.

Preferably, the condition is cancer, notably leukaemias including chronic myelogenous leukaemia and acute myeloid leukaemia, lymphomas, solid tumours, and PTEN-negative tumours including PTEN-negative haematological, breast, lung, endometrial, skin, brain and prostate cancers (where PTEN refers to "phosphatise and tensin homolog deleted on chromosome 10"). More preferably, the condition to be treated in a patient in need thereof by administering an effective amount of a disclosed compound is a disorder selected from rheumatoid arthritis, asthma, chronic obstructive pulmonary disease (COPD), multiple sclerosis, psoriasis and other inflammatory skin disorders, systemic lupus erythematosus, inflammatory bowel disease, and organ transplant rejection. For example, provided herein is a method of treating a patient suffering a disorder selected from the group consisting leukaemias (including e.g., chronic myelogenous leukaemia and acute myeloid leukaemia), lymphoma, a solid tumour cancer such as breast, lung, or prostate cancer, PTEN-negative tumours including PTEN-negative haematological, breast, lung, endometrial, skin, brain and prostate cancers (where PTEN refers to "phosphatise and tensin homolog deleted on chromosome 10") comprising administering an effective amount of a disclosed compound.

The invention will now be illustrated by the following Examples.

EXAMPLES

Synthesis of Intermediate X (a Precursor to the Compounds of Formula I)

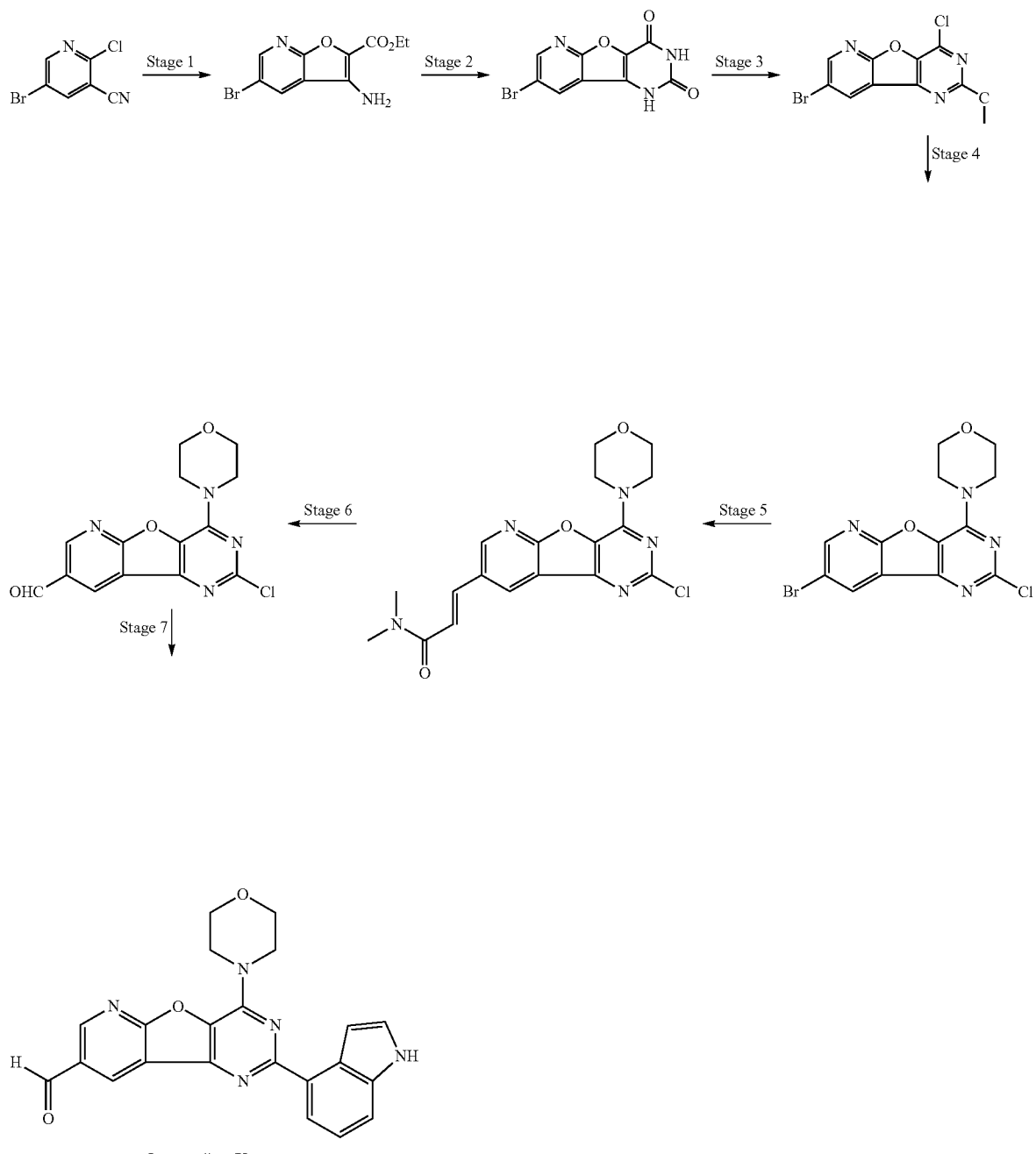

Intermediate X

Reagents and conditions: 1) K$_2$CO$_3$, ethyl glycolate, DMF, 115° C.; 2) (i) chlorosulfonyl isocyanate, CH$_2$Cl$_2$, 0-10° C. then rt (ii) water, 75° C. (iii) NaOH max temp 40° C.; 3) POCl$_3$, N,N-dimethylaniline, 107° C.; 4) morpholine, MeOH, rt; 5) N,N-dimethylacrylamide, PdCl$_2$(PPh$_3$)$_2$, NaOAc, DMF, 110° C.; 6) NaIO$_4$, OsO$_4$, THF, water, rt; 7) indole-4-boronic acid pinacol ester, PdCl$_2$(PPh$_3$)$_2$, sodium carbonate, dioxane, water, 102° C.

i. Ethyl-3-amino-5-bromofuro[2,3-b]pyridine-2-carboxylate

To a 10 L flask under N$_2$(g) was added 5-bromo-2-chloropyridine-3-carbonitrile (435 g, 2.0 mol, 1eq), DMF (2790 mL) and potassium carbonate (553 g, 4.0 mol, 2eq). This was followed by the addition of ethyl glycolate (208.2 mL, 2.2 mol, 1.1eq). The reaction mixture was heated to 115° C. overnight. Upon completion, the reaction mixture was cooled to rt and water (13.1 L) was added, this led to the formation of a precipitate. The mixture was stirred for 20 mins, then filtered. The resulting brown solid was dried at 50° C., slurried in Et$_2$O:heptane (9:1, 2.8 L) and filtered to give 405.6 g. Further purification via soxhlet extraction using TBME (4.5 L) yielded the product as a yellow solid (186 g, 34%). This procedure was repeated twice.

$^1$H NMR (400 MHz, CDCl$_3$) δ$_H$: 8.53 (d, J=2.0 Hz, 1H), 8.07 (d, J=2.0 Hz, 1H), 5.00 (br. s., 2H), 4.44 (q, J=7.0 Hz, 2H), 1.44 (t, J=7.0 Hz, 3H).

MS (ES$^+$) 309 (100%, [M+Na]$^+$), 307 (100%, [M+Na]$^+$).

ii. 12-Bromo-8-oxa-3,5,10-triazatricyclo[7.4.0.0$^{2,7}$]trideca-1(9),2(7),10,12-tetraene-4,6-dione To ethyl-3-amino-5-bromofuro[2,3-b]pyridine-2-carboxylate (239.0 g, 0.84 mol, 1eq) dissolved in CH$_2$Cl$_2$ (5.5 L) was added chlorosulfonyl isocyanate (87.6 mL, 1.0 mol, 1.2eq) dropwise at 0-10° C. The resulting reaction was stirred for 30 min, stripped to dryness and the resulting solid ground to a fine powder. Water (5.5 L) was added to the solid and the suspension was heated at 75° C. for 1 h. After cooling to rt, solid NaOH (335 g, 8.4 mol, 10eq) was added allowing the reaction to exotherm (maximum temperature 40° C.). The reaction was cooled to 0-10° C. and the pH adjusted to 5-6 using SM HCl (~1 L). The reaction was stirred for 30 mins, then filtered. The solid was washed with water (2.3 L) and pulled dry. Further drying in a vacuum oven at 40° C. yielded the product as a brown solid (193 g, 76%). This procedure was repeated twice.

$^1$H NMR (400 MHz, DMSO-d$_6$) δ$_H$: 12.01 (br. s., 1H), 11.58 (br. s, 1H), 8.72 (d, J=2.0 Hz, 1H), 8.59 (d, J=2.0 Hz, 1H).

MS (ES$^-$) 282 (100%, [M+H]$^+$).

iii. 12-Bromo-4,6-dichloro-8-oxa-3,5,10-triazatricyclo[7.4.0.0$^{2,7}$]trideca-1(9),2(7),3,5,10,12-hexaene To 12-bromo-8-oxa-3,5,10-triazatricyclo[7.4.0.0$^{2,7}$]trideca-1(9),2(7),10,12-tetraene-4,6-dione (387 g, 1.27 mol, 1eq) was added POCl$_3$ (6070 mL) and N,N-dimethylaniline (348 mL, 2.8 mol, 2.2eq). The mixture was heated at 107° C. for 10 h. Once cooled to rt, solvent was removed in vacuo azeotroping with toluene (3×3.9 L). The resulting residue was partitioned between CH$_2$Cl$_2$ (12.76 L) and water (3.9 L) and the phases separated. The organic phase was washed with water (2×3.9 L). The combined aqueous was back-extracted with CH$_2$Cl$_2$ (7.7 L) and the combined organics dried over MgSO$_4$, filtered and stripped to yield the product as brown solid (429 g, ~quant.).

$^1$H NMR (400 MHz, CDCl$_3$) δ$_H$: 8.78 (d, J=2.5 Hz, 1H), 8.72 (d, J=2.5 Hz, 1H).

iv. 12-bromo-4-chloro-6-(morpholin-4-yl)-8-oxa-3,5,10-triazatricyclo[7.4.0.0$^{2,7}$]trideca-1(9),2(7),3,5,10,12-hexaene To 12-bromo-4,6-dichloro-8-oxa-3,5,10-triazatricyclo[7.4.0.0$^{2,7}$]trideca-1(9),2(7),3,5,10,12-hexaene (419.3 g, 1.32 mol, 1eq) in MeOH (8588 mL) was added Morpholine (259 mL, 2.90 mol, 2.2eq) at rt. After stirring for 2 h, water (0.8 L) was added. It was then cooled to 0-5° C. and stirred for an additional 30 mins. The resulting solid was filtered, washed with water (5.2 L) and pulled dry. Further purification by silica gel column chromatography with CH$_2$Cl$_2$/EtOAc (1:0-9:1) yielded the desired product (419 g, 84%).

$^1$H NMR (400 MHz, CDCl$_3$) δ$_H$: 8.66 (d, J=2.0 Hz, 1H), 8.62 (d, J=2.0 Hz, 1H), 4.07-4.21 (m, 4H), 3.85-3.91 (m, 4H).

MS (ES$^+$) 393 (100%, [M+Na]$^+$), 391 (80%, [M+Na]$^+$).

v. (2E)-3-[4-Chloro-6-(morpholin-4-yl)-8-oxa-3,5,10-triazatricyclo[7.4.0.0$^{2,7}$]trideca-1(9),2(7),3,5,10,12-hexaen-12-yl]-N,N-dimethylprop-2-enamide To 12-bromo-4-chloro-6-(morpholin-4-yl)-8-oxa-3,5,10-triazatricyclo[7.4.0.0$^{2,7}$]trideca-1(9),2(7),3,5,10,12-hexaene (60 g, 0.15 mol, 1eq) was added N,N-dimethylacrylamide (16.7 mL, 0.15 mol, 1eq), PdCl$_2$(PPh$_3$)$_2$(3.4 g, 4.5 mmol, 0.03eq) and NaOAc (40 g, 0.45 mol, 3eq) in DMF (1.2 L). The reaction was heated at 110° C. for 7 h. This process was repeated 3 times and batches combined. Once cooled down to rt, solvent was removed in vacuo and the resulting residue was partitioned between CH$_2$Cl$_2$ (6.5 L) and water (5.5 L). The phases were separated and the aqueous phase was extracted with CH$_2$Cl$_2$ (2×4 L). The combined organics were washed with brine (2×4 L), dried over MgSO$_4$, filtered and stripped. The resulting solid was slurried in EtOAc/heptane (1:1, 0.8 L) for 30 mins, filtered, washed and washed with EtOAc/heptane (1:1, 2×450 mL). Further drying in a vacuum oven at 40° C. yielded the desired product as an orange solid (203.0 g, 86%).

$^1$H NMR (400 MHz, CDCl$_3$) δ$_H$: 8.70 (s, 2H), 7.82 (d, J=15.6 Hz, 1H), 7.07 (d, J=15.6 Hz, 1H), 4.11-4.19 (m, 4H), 3.85-3.93 (m, 4H), 3.22 (s, 3H), 3.11 (s, 3H).

MS (ES$^+$) 388 (100%, [M+H]$^+$).

vi. 4-Chloro-6-(morpholin-4-yl)-8-oxa-3,5,10-triazatricyclo[7.4.0.0$^{2,7}$]trideca-1(9),2(7),3,5,10,12-hexaene-12-carbaldehyde (2E)-3-[4-chloro-6-(morpholin-4-yl)-8-oxa-3,5,10-triazatricyclo[7.4.0.0$^{2,7}$]trideca-1(9),2(7),3,5,10,12-hexaen-12-yl]-N,N-dimethylprop-2-enamide (124.0 g, 0.39 mol, 1eq) was dissolved in THF (12.4 L) at 65° C. Once cooled to 35° C., water (4.1 L), NaIO$_4$ (205.4 g, 1.17 mol, 3eq) and OsO$_4$ (2.5 wt % in $^t$BuOH, 80.3 mL, 2%) were added. The reaction was stirred at rt for 60 h. The reaction was cooled to 0-5° C., stirred for 30 mins then filtered. The solid was washed with water (545 mL) and pulled dry. The crude product was combined with two further batches (2×118.3 g scale) and slurried in water (6.3 L) for 30 mins at rt. The solids were filtered, washed with water (1.6 L) and pulled dry. Further drying in a vacuum oven yielded the desired product as a pink solid (260 g, 88%)

¹H NMR (400 MHz, CDCl₃:MeOD, 9:1) $\delta_H$: 10.13 (s, 1H), 9.04 (d, J=2.0 Hz, 1H), 8.91 (d, J=2.0 Hz, 1H), 3.99-4.13 (m, 4H), 3.73-3.84 (m, 4H).

MS (ES⁺) 351 (100%, [M+MeOH+H]⁺).

vii. 4-(1H-Indol-4-yl)-6-(morpholin-4-yl)-8-oxa-3,5,10-triazatricyclo[7.4.0.0²,⁷]trideca-1(9),2,4,6,10,12-hexaene-12-carbaldehyde To 4-chloro-6-(morpholin-4-yl)-8-oxa-3,5,10-triazatricyclo[7.4.0.0²,⁷]trideca-1(9),2(7),3,5,10,12-hexaene-12-carbaldehyde (164.4 g, 0.52 mol, 1eq) was added indole-4-boronic acid pinacol ester (376.0 g, 1.55 mol, 3eq), PdCl₂(PPh₃)₂ (72.0 g, 0.10 mol, 2eq) and sodium carbonate (110.2 g, 1.04 mol, 2eq) in dioxane (16.4 L)/water (5.8 L). Reaction mixture was refluxed for 1 h. It was then cooled to 60-70° C. Water (9.8 L), brine (4.9 L) and EtOAc (9.5 L) were added. The phases were separated and the aqueous phase extracted with EtOAc (3×9.5 L) at 60-65° C. The combined organics were dried over MgSO₄, filtered and stripped. The resulting solid was slurried in CH₂Cl₂ (4.75 L) for 30 mins, filtered, washed with CH₂Cl₂ (3×238 mL) and pulled dry. Further drying in a vacuum oven at 40° C. yielded Intermediate X as a yellow solid (135.7 g, 66%).

¹H NMR (300 MHz, CDCl₃) $\delta_H$: 11.27 (br. s, 1H), 10.26 (s, 1H), 9.16 (d, J=2.3 Hz, 1H), 9.11 (d, J=2.3 Hz, 1H), 8.18 (d, J=7.5 Hz, 1H), 7.58-7.67 (m, 2H), 7.49 (t, J=2.8 Hz, 1H), 7.23 (t, J=7.7 Hz, 1H), 4.08-4.16 (m, 4H), 3.83-3.90 (m, 4H).

MS (ES⁺) 432.0 (100%, [M+MeOH+H]⁺).

Synthesis of Examples of the Present Invention

Example A 4-(1H-Indol-4-yl)-6-(morpholin-4-yl)-12-[(1S,4S)-2-oxa-5-azabicyclo[2.2.1]heptan-5-ylmethyl]-8-oxa-3,5,10-triazatricyclo[7.4.0.0²,⁷]trideca-1(13),2(7),3,5,9,11-hexaene

A

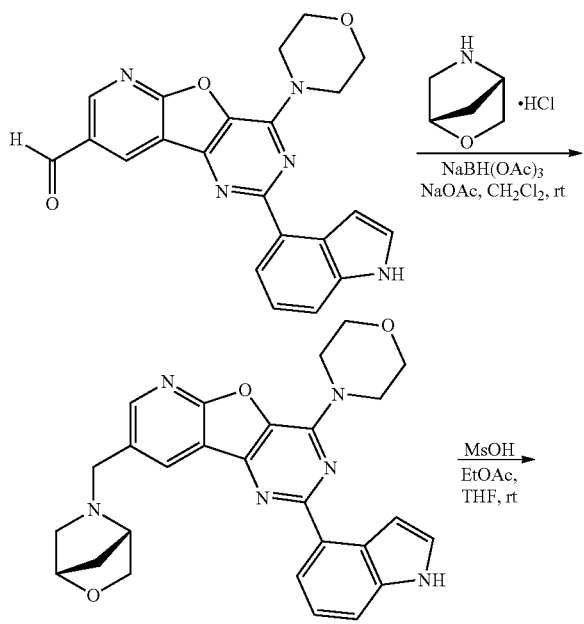

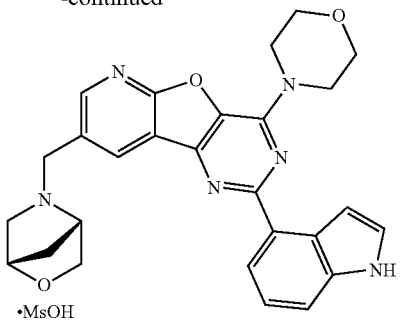

·MsOH

To a suspension of intermediate X (7.00 g, 17.53 mmol, 1eq), (1S,4S)-2-oxa-5-azabicyclo[2.2.1]heptane hydrochloride (7.13 g, 52.58 mmol, 3eq) and NaOAc (4.31 g, 52.58 mmol, 3eq) in anhydrous CH₂Cl₂ (150 mL) was added NaBH(OAc)₃ (7.43 g, 35.06 mmol, 2eq). The reaction mixture was stirred at rt overnight. Then, it was partitioned with 1N NaOH (100 mL) and extracted with CH₂Cl₂ (3×200 mL). The combined organic extracts were washed with brine (50 mL) then dried over MgSO₄ and the solvent was removed in vacuo. Purification by silica gel column chromatography with EtOAc/MeOH (1:0-7:1) yielded the product A as a white solid (6.02 g, 71%).

¹H NMR (300 MHz, CDCl₃) $\delta_H$: 8.65 (d, J=2.1 Hz, 1H), 8.58 (d, J=2.1 Hz, 1H), 8.37 (br. s., 1H), 8.24 (dd, J=7.5, 0.9 Hz, 1H), 7.62 (td, J=2.6, 0.8 Hz, 1H), 7.53 (d, J=8.1 Hz, 1H), 7.37-7.41 (m, 1H), 7.31-7.37 (m, 1H), 4.47 (s, 1H), 4.22-4.30 (m, 4H), 4.18 (d, J=8.1 Hz, 1H), 3.98 (d, J=2.3 Hz, 2H), 3.91-3.97 (m, 4H), 3.70 (dd, J=7.9, 1.7 Hz, 1H), 3.53 (s, 1H), 2.94 (dd, J=10.0, 1.5 Hz, 1H), 2.64 (d, J=10.2 Hz, 1H), 1.97 (dd, J=9.8, 1.9 Hz, 1H), 1.80 (dt, J=9.8, 1.1 Hz, 1H).

MS (ES⁺) 483.1 (100%, [M+H]⁺).

4-(1H-Indol-4-yl)-6-(morpholin-4-yl)-12-[(1S,4S)-2-oxa-5-azabicyclo[2.2.1]heptan-5-ylmethyl]-8-oxa-3,5,10-triazatricyclo[7.4.0.0²,⁷]trideca-1(13),2(7),3,5,9,11-hexaene; methanesulfonic acid A (5.98 g, 12.38 mmol, 1eq) was dissolved in hot EtOAc (1 L) and THF (200 mL). Once cooled down to rt, a solution of MsOH (884 µL, 13.6 mmol, 1.1eq) in EtOAc (5 mL) was added slowly. An instant yellow precipitate formed. The suspension was shaken vigorously for 10 s then left to stand at rt overnight. As solid settled, excess supernatant was decanted off (200 mL), then EtOAc was added (200 mL). The suspension was shaken again and left to stand for 1 h. This operation was repeated twice, then the solvent was removed in vacuo. The salt form of A was obtained as a yellow solid (6.50 g, 91%).

¹H NMR (300 MHz, DMSO-d₆) $\delta_H$: 11.33 (br. s., 1H), 9.69-10.24 (m, 1H), 9.05 (d, J=2.1 Hz, 1H), 8.79-8.93 (m, 1H), 8.19 (d, J=7.5 Hz, 1H), 7.54-7.62 (m, 2H), 7.50 (t, J=2.7 Hz, 1H), 7.24 (t, J=7.7 Hz, 1H), 4.64-4.89 (m, 2H), 4.47-4.61 (m, 2H), 4.14 (m, 4H), 3.94-4.00 (m, 2H), 3.83-3.91 (m, 4H), 3.72-3.83 (m, 1H), 3.29-3.46 (m, 2H), 2.33 (s, 4H), 2.02-2.15 (m, 1H).

MS (ES⁺) 483.1 (100%, [M-MsOH+H]⁺).

Example B 4-(1H-Indol-4-yl)-6-(morpholin-4-yl)-12-(2-oxa-7-azaspiro[3.5]nonan-7-ylmethyl)-8-oxa-3,5,10-triazatricyclo[7.4.0.0²,⁷]trideca-1(13),2(7),3,5,9,11-hexaene

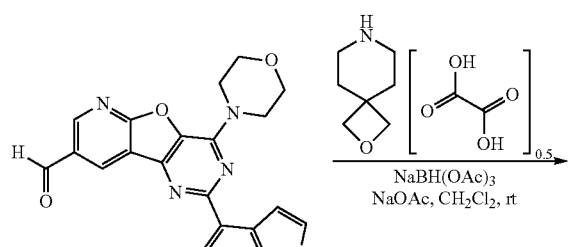

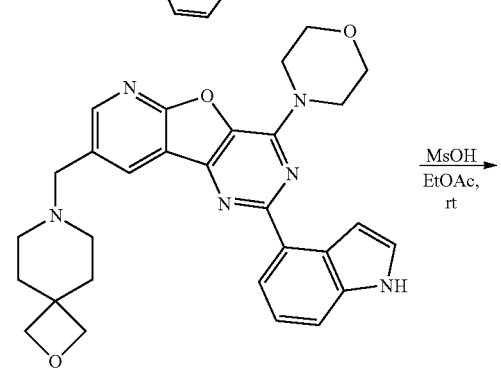

To a suspension of intermediate X (3.108 g, 7.78 mmol 1eq), 2-oxa-7-azaspiro[3.5]nonane hemioxalate (4.02 g, 23.3 mmol, 3eq) and NaOAc (1.91 g, 23.3 mmol, 3eq) in anhydrous $CH_2Cl_2$ (280 mL) was added $NaBH(OAc)_3$ (3.30 g, 15.6 mmol, 2eq). The reaction mixture was stirred at rt overnight. Then, it was partitioned with 1N NaOH (150 mL) and extracted with $CH_2Cl_2$ (2×100 mL). The combined organic extracts were washed with 50% brine (100 mL) then dried over $MgSO_4$ and the solvent was removed in vacuo. Purification by silica gel column chromatography with EtOAc/MeOH (1:0-8:1) yielded the product B as an off-white solid (3.154 g, 79%).

¹H NMR (300 MHz, CDCl₃) δ_H: 8.59 (d, J=2.1 Hz, 1H), 8.53 (d, J=1.9 Hz, 1H), 8.41 (br. s., 1H), 8.24 (dd, J=7.4, 0.8 Hz, 1H), 7.61 (t, J=2.3 Hz, 1H), 7.53 (d, J=8.1 Hz, 1H), 7.37-7.41 (m, 1H), 7.34 (t, J=7.9 Hz, 1H), 4.43 (s, 4H), 4.22-4.30 (m, 4H), 3.86-4.00 (m, 4H), 3.68 (s, 2H), 2.23-2.59 (m, 4H), 1.83-2.00 (m, 4H).

MS (ES⁺) 511.1 (100%, [M+H]⁺).

4-(1H-Indol-4-yl)-6-(morpholin-4-yl)-12-(2-oxa-7-azaspiro[3.5]nonan-7-ylmethyl)-8-oxa-3,5,10-triazatricyclo[7.4.0.0²,⁷]trideca-1(13),2(7),3,5,9,11-hexaene; methanesulfonic acid To a solution of B (2.987 g, 5.854 mmol, 1eq) in EtOAc (1.2 L, heat to 70° C. for 5 min to dissolve) at rt was added a solution of MsOH (590 μL, 6.14 mmol, 1.05eq) in EtOAc (16 mL). A yellow precipitate formed instantly. The suspension was shaken vigorously for 20 s then left to stand at rt overnight. The excess supernatant was decanted off (600 mL), then EtOAc was added (500 mL). The suspension was shaken again and left to stand for 1 h before another 500 mL of excess supernatant was decanted off. The solvent was removed in vacuo to give the salt form of F as a yellow solid (3.230 g, 91%).

¹H NMR (300 MHz, DMSO-d₆) δ_H: 11.33 (br. s., 1H), 9.45 (br. s., 1H), 8.90 (d, J=1.9 Hz, 1H), 8.72 (d, J=1.9 Hz, 1H), 8.19 (d, J=7.3 Hz, 1H), 7.41-7.69 (m, 3H), 7.23 (t, J=7.8 Hz, 1H), 4.58 (d, J=3.8 Hz, 2H), 4.39 (s, 2H), 4.29 (s, 2H), 4.03-4.22 (m, 4H), 3.81-3.97 (m, 4H), 3.40 (d, J=12.1 Hz, 2H), 2.88-3.13 (m, 2H), 2.33 (s, 3H), 2.26 (d, J=13.9 Hz, 2H), 1.69-1.91 (m, 2H).

MS (ES⁺) 511.1 (100%, [M-MsOH+H]⁺).

Example C 4-(1H-Indol-4-yl)-6-(morpholin-4-yl)-12-{8-oxa-3-azabicyclo[3.2.1]octan-3-ylmethyl}-8-oxa-3,5,10-triazatricyclo[7.4.0.0²,⁷]trideca-1(13),2(7),3,5,9,11-hexaene

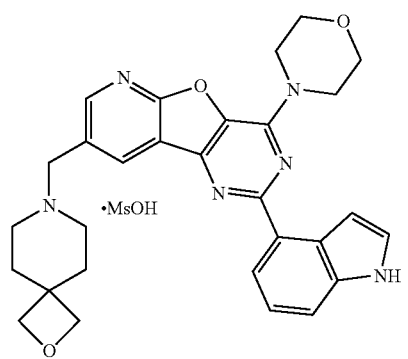

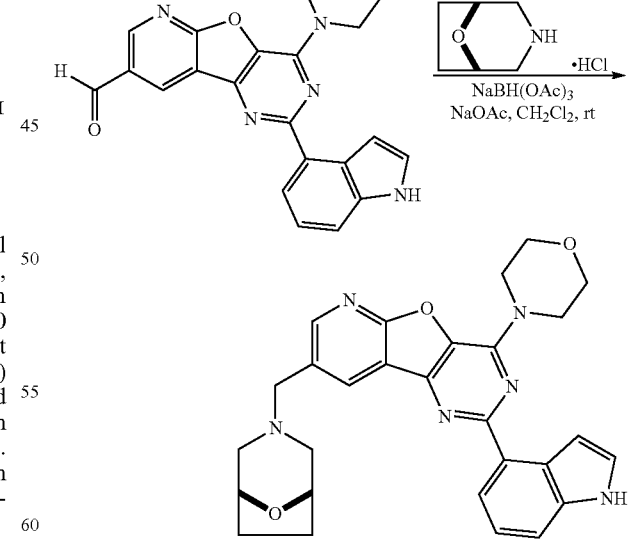

To a suspension of intermediate X (100 mg, 0.25 mmol, 1eq), 8-oxa-3-azabicyclo[3.2.1]octane hydrochloride (112 mg, 0.75 mmol, 3eq) and NaOAc (62 mg, 0.75 mmol, 3eq) in anhydrous $CH_2Cl_2$ (10 mL) was added $NaBH(OAc)_3$ (106 mg, 0.50 mmol, 2eq). The reaction mixture was stirred at rt overnight. Then, it was partitioned with 1N NaOH (10 mL), extracted with CH$_2$Cl$_2$ (3×10 mL). The combined organic extracts were washed with brine (10 mL) then dried over MgSO$_4$ and the solvent was removed in vacuo. Purification by silica gel column chromatography with EtOAc/MeOH (1:0-49:1) yielded the product C as an off white solid (116 mg, 93%).

$^1$H NMR (300 MHz, CDCl$_3$) δ$_H$: 8.56 (d, J=3.6 Hz, 2H), 8.35 (br. s., 1H), 8.24 (d, J=7.5 Hz, 1H), 7.58-7.66 (m, 1H), 7.51-7.57 (m, 1H), 7.31-7.44 (m, 2H), 4.30-4.38 (m, 2H), 4.23-4.30 (m, 4H), 3.89-4.01 (m, 4H), 3.68 (s, 2H), 2.61 (d, J=10.7 Hz, 2H), 2.40-2.52 (m, 2H), 1.96-2.09 (m, 2H), 1.83-1.95 (m, 2H). MS (ES$^+$) 497.1 (100%, [M+H]$^+$).

Example D 4-(1H-Indol-4-yl)-12-({2-methyl-2,8-diazaspiro[4.5]decan-8-yl}methyl)-6-(morpholin-4-yl)-8-oxa-3,5,10-triazatricyclo[7.4.0.0$^{2,7}$]trideca-1(13),2(7),3,5,9,11-hexaene

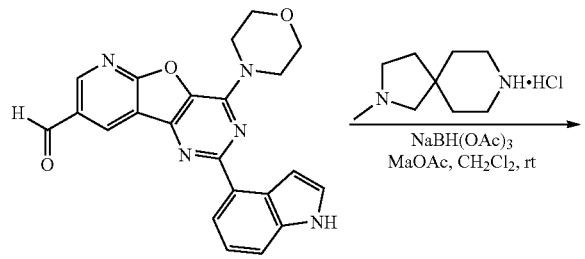

To a suspension of intermediate X (1.02 g, 2.55 mmol, 1eq), 2-methyl-2,8-diazaspiro[4.5]decane hydrochloride (1.46 g, 7.66 mmol, 3eq) and NaOAc (628 mg, 7.66 mmol, 3eq) in anhydrous CH$_2$Cl$_2$ (100 mL) was added NaBH(OAc)$_3$ (1.08 g, 5.1 mmol, 2eq). The reaction mixture was stirred at rt overnight. Then, it was partitioned with 1N NaOH (30 mL) and extracted with CH$_2$Cl$_2$ (3×50 mL). The combined organic extracts were washed with brine (10 mL) then dried over MgSO$_4$ and the solvent was removed in vacuo. Purification by silica gel column chromatography with CH$_2$Cl$_2$/MeOH (0:1-4:1) yielded the product D as a white solid (890 mg, 65%).

$^1$H NMR (300 MHz, CDCl$_3$) δ$_H$: 8.60 (d, J=2.1 Hz, 1H), 8.54 (d, J=2.1 Hz, 1H), 8.39 (br. s., 1H), 8.24 (dd, J=7.4, 0.8 Hz, 1H), 7.62 (t, J=2.3 Hz, 1H), 7.53 (d, J=8.1 Hz, 1H), 7.38 (t, J=2.8 Hz, 1H), 7.30-7.37 (m, 1H), 4.21-4.31 (m, 4H), 3.89-3.99 (m, 4H), 3.69 (s, 2H), 2.59 (t, J=6.8 Hz, 2H), 2.38-2.50 (m, 5H), 2.35 (s, 3H), 1.54-1.73 (m, 7H).

MS (ES$^+$) 538.2 (100%, [M+H]$^+$).

4-(1H-Indol-4-yl)-12-({2-methyl-2,8-diazaspiro[4.5]decan-8-yl}methyl)-6-(morpholin-4-yl)-8-oxa-3,5,10-triazatricyclo[7.4.0.0$^{2,7}$]trideca-1(13),2(7),3,5,9,11-hexaene; bis(methanesulfonic acid)

Compound D (821 mg, 1.52 mmol, 1eq) was dissolved in hot EtOAc (400 mL). Once cooled down to rt, a solution of MsOH (218 μL, 3.36 mmol, 2.2eq) in EtOAc (5 mL) was added slowly. An instant yellow precipitate formed. The suspension was shaken vigorously for 10 s then left to stand at rt overnight. As solid settled, excess supernatant was decanted off (200 mL), then EtOAc was added (200 mL). The suspension was shaken again and left to stand for 1 h. This operation was repeated twice, then the solvent was removed in vacuo. The salt form of D was obtained as a yellow solid (1.037 g, 93%).

$^1$H NMR (300 MHz, DMSO-d$_6$) δ$_H$: 11.32 (br. s., 1H), 9.46-10.03 (m, 2H), 8.93 (d, J=2.1 Hz, 1H), 8.76 (d, J=1.7 Hz, 1H), 8.19 (dd, J=7.4, 0.7 Hz, 1H), 7.53-7.60 (m, 2H), 7.50 (t, J=2.6 Hz, 1H), 7.24 (t, J=7.8 Hz, 1H), 4.63 (br. s., 2H), 4.10-4.20 (m, 4H), 3.82-3.91 (m, 5H), 3.54-3.77 (m, 2H), 3.36-3.51 (m, 2H), 3.05-3.25 (m, 3H), 2.89-3.03 (m, 1H), 2.80-2.89 (m, 3H), 2.36 (s, 6H), 2.02-2.17 (m, 1H), 1.65-1.95 (m, 4H).

MS (ES$^+$) 538.2 (100%, [M−2MsOH+H]$^+$).

Example E 4-(1H-Indol-4-yl)-12-({7-methyl-2,7-diazaspiro[4.4]nonan-2-yl}methyl)-6-(morpholin-4-yl)-8-oxa-3,5,10-triazatricyclo[7.4.0.0$^{2,7}$]trideca-1(13),2(7),3,5,9,11-hexaene

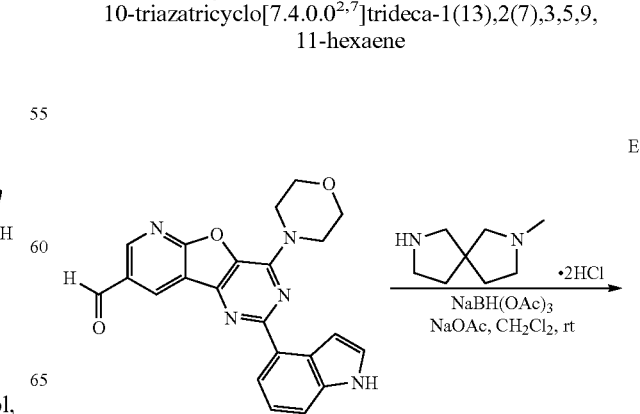

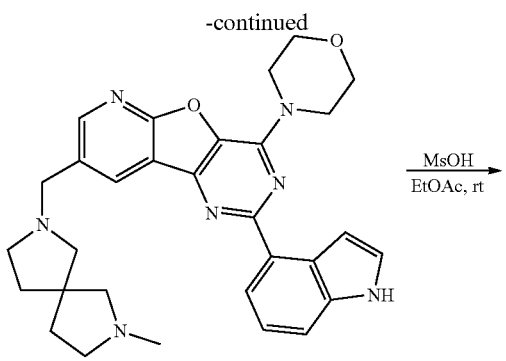

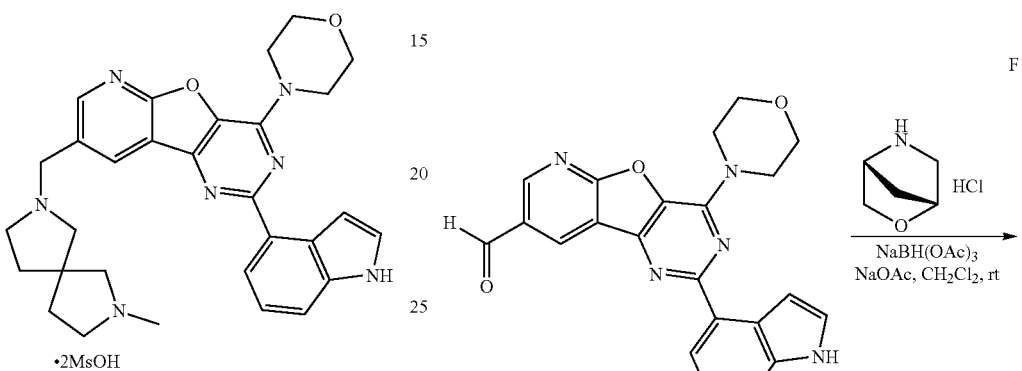

To a suspension of intermediate X (250 mg, 0.63 mmol, 1eq), 2-methyl-2,7-diazaspiro[4,4]nonane dihydrochloride (400 mg, 1.87 mmol, 3eq) and NaOAc (305 mg, 3.70 mmol, 6eq) in anhydrous CH$_2$Cl$_2$ (20 mL) was added NaBH(OAc)$_3$ (265 mg, 1.25 mmol, 2eq). The reaction mixture was stirred at rt overnight. Then, it was partitioned with 1N NaOH (10 mL), extracted with CH$_2$Cl$_2$ (3×10 mL) and EtOAc (10 mL). The combined organic extracts were washed with brine (10 mL) then dried over MgSO$_4$ and the solvent was removed in vacuo. Purification by silica gel column chromatography with CH$_2$Cl$_2$/MeOH (0:1-4:1) yielded the product E as a white solid (169 mg, 52%).

$^1$H NMR (300 MHz, CDCl$_3$) $\delta_H$: 8.58 (d, J=2.1 Hz, 1H), 8.53 (d, J=2.1 Hz, 1H), 8.48 (br. s., 1H), 8.23 (dd, J=7.4, 0.8 Hz, 1H), 7.63 (t, J=2.2 Hz, 1H), 7.53 (d, J=7.9 Hz, 1H), 7.39 (t, J=2.7 Hz, 1H), 7.29-7.36 (m, 1H), 4.21-4.30 (m, 4H), 3.89-3.99 (m, 4H), 3.72-3.85 (m, 2H), 2.49-2.83 (m, 8H), 2.45 (s, 3H), 1.81-2.06 (m, 4H).

MS (ES$^+$) 524.1 (100%, [M+H]$^+$).

4-(1H-Indol-4-yl)-12-({7-methyl-2,7-diazaspiro[4.4]nonan-2-yl}methyl)-6-(morpholin-4-yl)-8-oxa-3,5,10-triazatricyclo[7.4.0.0$^2$]trideca-1(13),2(7),3,5,9,11-hexaene; bis(methanesulfonic acid)

Compound E (129 mg, 0.25 mmol, 1eq) was dissolved in hot EtOAc (50 mL). Once cooled down to rt, a solution of MsOH (35 µL, 0.54 mmol, 2.2eq) in EtOAc (2 mL) was added slowly. An instant yellow precipitate formed. The suspension was shaken vigorously for 10 s then left to stand at rt overnight. As solid settled, excess supernatant was decanted off (20 mL), then EtOAc was added (20 mL). The suspension was shaken again and left to stand for 1 h. This operation was repeated twice, then the solvent was removed in vacuo. The salt form of E was obtained as a yellow solid (173 mg, 98%).

$^1$H NMR (300 MHz, DMSO-d$_6$) $\delta_H$: 11.33 (br. s., 1H), 10.39 (br. s., 1H), 9.72-10.12 (m, 1H), 8.73-9.09 (m, 2H), 8.19 (d, J=7.5 Hz, 1H), 7.41-7.63 (m, 3H), 7.24 (t, J=7.8 Hz, 1H), 4.53-4.87 (m, 2H), 4.10-4.22 (m, 4H), 3.79-3.93 (m, 4H), 3.32-3.77 (m, 6H), 2.99-3.29 (m, 2H), 2.78-2.89 (m, 3H), 2.36 (s, 6H), 1.87-2.22 (m, 3H).

MS (ES$^+$) 524.5 (100%, [M−2MsOH+H]$^+$).

Example F 4-(1H-Indol-4-yl)-6-(morpholin-4-yl)-12-[(1R,4R)-2-oxa-5-azabicyclo[2.2.1]heptan-5-ylmethyl]-8-oxa-3,5,10-triazatricyclo[7.4.0.0$^{2,7}$]trideca-1(13),2(7),3,5,9,11-hexaene To a suspension of intermediate X (200 mg, 0.50 mmol, 1eq), (1R,4R)-2-oxa-5-azabicyclo[2.2.1]heptane hydrochloride (204 mg, 1.50 mmol, 3eq) and NaOAc (123 mg, 1.5 mmol, 3eq) in anhydrous CH$_2$Cl$_2$ (10 mL) was added NaBH(OAc)$_3$ (160 mg, 0.76 mmol, 2eq). The reaction mixture was stirred at rt overnight. Then, it was partitioned with 1N NaOH (20 mL) and extracted with CH$_2$Cl$_2$ (3×20 mL). The combined organic extracts were passed through a phase separator and the solvent was removed in vacuo. Purification by silica gel column chromatography with EtOAc/MeOH (1:0-9:1) yielded the product F as a white solid (141.1 mg, 59%).

$^1$H NMR (400 MHz, CDCl$_3$) $\delta_H$: 8.64 (d, J=2.1 Hz, 1H), 8.57 (d, J=2.1 Hz, 1H), 8.35 (br. s., 1H), 8.23 (dd, J=7.5, 0.9

Hz, 1H), 7.62 (m, 1H), 7.53 (d, J=8.1 Hz, 1H), 7.36-7.39 (m, 1H), 7.31-7.36 (m, 1H), 4.46 (s, 1H), 4.25 (m, 4H), 4.18 (d, J=8.1 Hz, 1H), 3.97 (d, J=2.3 Hz, 2H), 3.93-3.97 (m, 4H), 3.68 (dd, J=7.9, 1.7 Hz, 1H), 3.53 (s, 1H), 2.93 (dd, J=10.0, 1.5 Hz, 1H), 2.62 (d, J=10.2 Hz, 1H), 1.95 (dd, J=9.8, 1.9 Hz, 1H), 1.79 (dt, J=9.8, 1.1 Hz, 1H).

MS (ES$^+$) 483.1 (100%, [M+H]$^+$).

4-(1H-Indol-4-yl)-6-(morpholin-4-yl)-12-[(1R,4R)-2-oxa-5-azabicyclo[2.2.1]heptan-5-ylmethyl]-8-oxa-3,5,10-triazatricyclo[7.4.0.0$^{2,7}$]trideca-1(13),2(7),3,5,9,11-hexaene; methanesulfonic acid Compound F (141 mg, 0.29 mmol, 1eq) was dissolved in hot EtOAc (100 mL) then treated with 0.87 ml of a 0.308M MsOH solution in EtOAc under vigorously swirling. The mixture was set aside overnight. The excess supernatant was decanted (using a small Pasteur pipette) and more EtOAc (50 ml) was added. The suspension was once again shaken vigorously then left to stand at rt overnight. The excess supernatant was once more decanted and the solvent was removed in vacuo. The resulting solid was dried in a vacuum oven at 40° C. The salt form of F was obtained as a yellow solid (160 mg, 95%).

$^1$H NMR (400 MHz, DMSO-d$_6$) δ$_H$: 11.33 (br. s., 1H), 9.65-10.16 (m, 1H), 9.05 (d, J=2.0 Hz, 1H), 8.83-8.90 (m, 1H), 8.20 (d, J=7.3 Hz, 1H), 7.58-7.61 (m, 1H), 7.56 (d, J=7.8 Hz, 1H), 7.51 (t, J=2.8 Hz, 1H), 7.23 (t, J=7.7 Hz, 1H), 4.82 (dd, J=13.1, 4.5 Hz, 1H), 4.65-4.76 (m, 1H), 4.50-4.59 (m, 2H), 4.11-4.19 (m, 4H), 3.99 (d, J=9.6 Hz, 1H), 3.88 (t, J=4.5 Hz, 4H), 3.78 (dd, J=9.5, 1.4 Hz, 1H), 3.31-3.38 (m, 2H), 2.52-2.57 (m, 1H), 2.30 (s, 3H), 2.02-2.18 (m, 1H).

MS (ES$^+$) 483.2 (100%, [M-MsOH+H]$^+$).

Example G 4-(1H-Indol-4-yl)-6-(morpholin-4-yl)-12-{6-oxa-1-azaspiro[3.3]heptan-1-ylmethyl}-8-oxa-3,5,10-triazatricyclo[7.4.0.0$^{2,7}$]trideca-1(13),2(7),3,5,9,11-hexaene

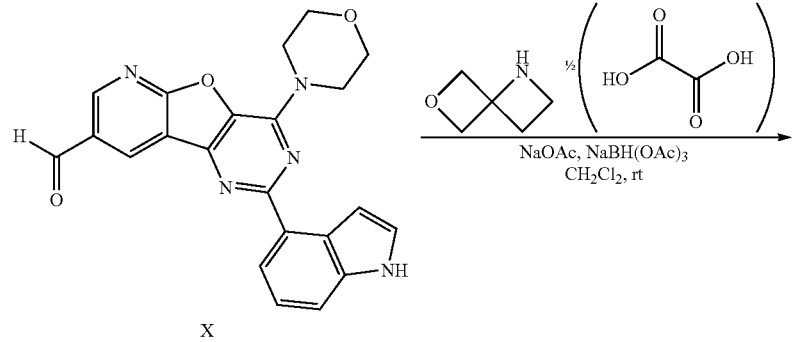

X

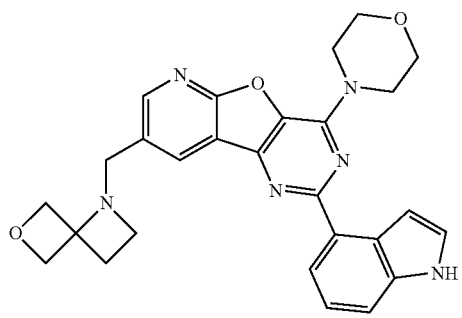

G

Intermediate X (125 mg, 0.31 mmol), 6-oxa-1-azaspiro[3.3]heptane hemioxalate (134 mg, 0.93 mmol, 3eq) and NaOAc (76 mg, 0.93 mmol, 3eq) were suspended in $CH_2Cl_2$ (16 mL) at rt. The mixture was stirred for 15 mins then $NaBH(OAc)_3$ (131 mg, 0.62 mmol, 2eq) was added. The resulting suspension was stirred at rt overnight. The reaction mixture was then partitioned with 0.5 N NaOH (8 mL) and extracted with $CH_2Cl_2$ (2×10 mL). The combined organics were washed with 50% brine (5 mL) then dried over $MgSO_4$ and the solvent was removed in vacuo. The residue was dissolved in DMSO (2 mL) and purified by basic preparative LCMS to yield G as a white solid (48 mg, 32%).

$^1H$ NMR (DMSO-$d_6$) $\delta_H$: 11.30 (br s, 1H), 8.62 (s, 2H), 8.18 (d, J=7.6 Hz, 1H), 7.51-7.58 (m, 2H), 7.46-7.51 (m, 1H), 7.22 (t, J=7.7 Hz, 1H), 4.89 (d, J=7.6 Hz, 2H), 4.55 (d, J=7.3 Hz, 2H), 4.08-4.17 (m, 4H), 4.03 (s, 2H), 3.81-3.91 (m, 4H), 3.03 (t, J=6.7 Hz, 2H), 2.32 (t, J=6.7 Hz, 2H).

MS (ES$^+$) 483.3 (100%, [M+H]$^+$).

Biological Data

Fold form selectivity inhibition data against PI3K isoforms, as determined using a HTRF biochemical assay, is listed below.

| | Fold IC$_{50}$ | | | |
|---|---|---|---|---|
| Example | p110β/p110α | p110β/p110γ | p110δ/p110α | p110δ/p110γ |
| A | * | * | ** | ** |
| B | ** | ** | ** | ** |
| D | ** | ** | ** | ** |
| E | ** | ** | ** | ** |

Key:
* = ≥10x ≥ 50x
** = ≥50x

| | IC$_{50}$ (nM) PI3K | | | |
|---|---|---|---|---|
| Example | p110α | p110β | p110δ | p110γ |
| G | * | * | * | ** |

Key:
**** ≥10 uM;
*** ≤10 uM ≥ 1 uM;
** ≤1 uM ≥ 500 nM;
* ≤500 nM

Rodent Pharmacokinetic Comparative Data

Disclosed compounds have increased bioavailability and reduced clearance (data below for mice).

Example A

The following protocol was used to determine oral bioavailability and clearance, and the results are shown below:
Species=male mouse;
Strain=CD1;
n=3 male mice per time point per route;
Terminal blood sampling at 8 time points (5 min, 10 min, 0.5 hr, 1 hr, 3 hr, 6 hr, 8 hr and, 24 hr);
Collection of plasma, bio-analysis and report of AUC, AUMC, Vss, CL, half-life, MRT and bioavailability.
Formulation: 10% DMSO, 90% Saline
Dosing: 10 mg/kg P.O. and 5 mg/kg I.V.

Plasma PK Summary:

| Parameters - IV, 5 mg/kg | Value - Mesylate Salt |
|---|---|
| $t_{1/2}$ (hr) | 1.3 |
| $T_{max}$ (hr) | 0.08 |
| $C_{max}$ (ng/mL) | 2640 |
| AUC$_{last}$ (hr*ng · mL) | 3905 |
| AUC$_{all}$ (hr*ng/mL) | 3905 |
| AUC$_{inf}$ (hr*ng/mL) | 3946 |
| Clearance (mL/hr/Kg) | 1267 |
| Vd (mL/Kg) | 2441 |

| Parameters - PO, 10 mg/kg | Value - Mesylate Salt |
|---|---|
| $t_{1/2}$ (hr) | 1.3 |
| $T_{max}$ (hr) | 1.00 |
| $C_{max}$ (ng/mL) | 1973 |
| AUC$_{last}$ (hr*ng/mL) | 5625 |
| AUC$_{all}$ (hr*ng/mL) | 5625 |
| AUC$_{inf}$ (hr* ng/mL) | 5822 |
| F | 73.77% |

Example A

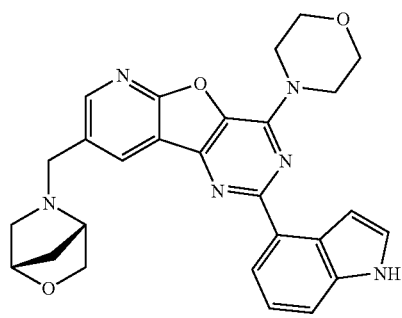

Oral bioavailability (F) = 74%
Clearance = 21 mL/min/kg

Example B

The following protocol was used to determine oral bioavailability and clearance, and the results are shown below:
Species=male mouse;
Strain=Balb/c;
18 male mice were divided into two groups Group 1 (3 mg/kg: I.V.), Group 2 (10 mg/kg; P.O.) with each group comprising of nine mice;
Blood samples (approximately 60 µL) were collected from retro orbital plexus under light isoflurane anesthesia such that the samples were obtained at pre-dose, 0.08, 0.25, 0.5, 1, 2, 4, 8 and 24 hr (I.V.) and pre-dose, 0.25, 0.5, 1, 2, 4, 6, 8 and 24 hr (P.O.);
The blood samples were collected from a set of three mice at each time point in labeled micro centrifuge tube containing K2EDTA as anticoagulant;
Plasma samples were separated by centrifugation of whole blood and stored below −70° C. until bioanalysis;
All samples were processed for analysis by protein precipitation using acetonitrile (ACN) and analyzed with fit for purpose LC/MS/MS method (LLOQ: 2.02 ng/mL);

Pharmacokinetic parameters were calculated using the non-compartmental analysis tool of Phoenix WinNonlin (Version 6.3).

Formulation:

Animals in Group 1 were administered intravenously with Example B solution formulation in 20% Propylene Glycol, 50% of PEG 400 and 30% of (20% HPβCD in water) via tail vein at a dose of 3 mg/kg.

Animals in Group 2 were administered with oral solution formulation of Example B in 20% Propylene Glycol, 50% of PEG 400 and 30% of (20% HPβCD in water) at a dose of 10 mg/kg;

Dosing: 10 mg/kg P.O. and 3 mg/kg I.V.

Plasma PK Summary:

| Parameters - IV, 3 mg/kg | Value - Mesylate Salt |
|---|---|
| $t_{1/2}$ (hr) | 1.23 |
| $C_{max}$ (ng/mL) | 621.42 |
| $AUC_{last}$ (hr*ng · mL) | 1512.20 |
| $AUC_{inf}$ (hr*ng/mL) | 1512.20 |
| Clearance (mL/hr/Kg) | 1983.6 |
| Vss (L/Kg) | 5.51 |

| Parameters - PO, 10 mg/kg | Value - Mesylate Salt |
|---|---|
| $T_{max}$ (hr) | 1.00 |
| $C_{max}$ (ng/mL) | 779.58 |
| $AUC_{last}$ (hr*ng/mL) | 3725.56 |
| $AUC_{inf}$ (hr* ng/mL) | 4103.86 |
| F | 74% |

Example B

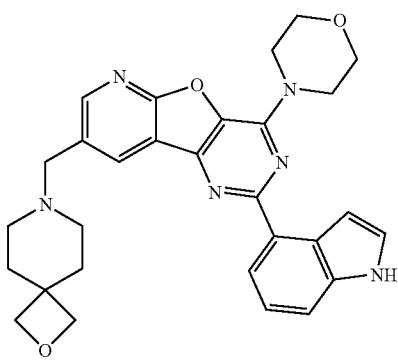

Oral bioavailability (F) = 74%
Clearance = 33 mL/min/kg

Example G

The following protocol was used to determine oral bioavailability and clearance, and the results are shown below:
Species=male mouse;
Strain=Balb/c;
18 male mice were divided into two groups Group 1 (3 mg/kg; I.V.), Group 2 (10 mg/kg; P.O.) with each group comprising of nine mice;
Blood samples (approximately 60 μL) were collected from retro orbital plexus under light isoflurane anesthesia such that the samples were obtained at pre-dose, 0.08, 0.25, 0.5, 1, 2, 4, 8 and 24 hr (I.V.) and pre-dose, 0.25, 0.5, 1, 2, 4, 6, 8 and 24 hr (P.O.);
The blood samples were collected from set of three mice at each time point in labeled micro centrifuge tube containing K2EDTA as anticoagulant;
Plasma samples were separated by centrifugation of whole blood and stored below −70° C. until bioanalysis;
All samples were processed for analysis by protein precipitation using acetonitrile (ACN) and analyzed with fit for purpose LC/MS/MS method (LLOQ: 2.47 ng/mL);
Pharmacokinetic parameters were calculated using the non-compartmental analysis tool of Phoenix WinNonlin (Version 6.3).

Formulation:

Animals in Group 1 were administered intravenously with Example G solution formulation in 5% NMP, 5% solutol HS-15 in 90% HPβCD solution (20% HPβCD in RO water) at 3 mg/kg dose.

Animals in Group 2 were administered orally with 10 mg/kg solution formulation of Example G in 5% NMP, 5% solutol HS-15 in 90% HPβCD solution (20% HPβCD in RO water)

Dosing: 10 mg/kg P.O. and 3 mg/kg I.V.

| Parameters - IV, 3 mg/kg | Value - Mesylate Salt |
|---|---|
| $t_{1/2}$ (hr) | 0.59 |
| $C_{max}$ (ng/mL) | 2205.80 |
| $AUC_{last}$ (hr*ng · mL) | 1918.37 |
| $AUC_{inf}$ (hr*ng/mL) | 1935.24 |
| Clearance (mL/hr/Kg) | 1550.4 |
| Vss (L/Kg) | 1.25 |

| Parameters - PO, 10 mg/kg | Value - Mesylate Salt |
|---|---|
| $T_{max}$ (hr) | 0.25 |
| $C_{max}$ (ng/mL) | 833.35 |
| $AUC_{last}$ (hr*ng/mL) | 1892.53 |
| $AUC_{inf}$ (hr* ng/mL) | 2144.97 |
| F | 30% |

Example G

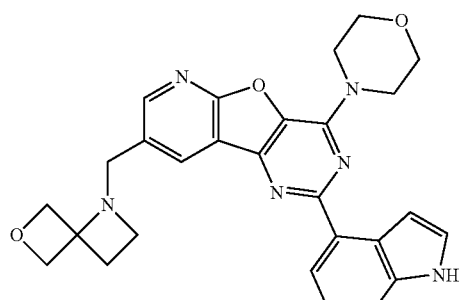

Oral bioavailability (F) = 30%
Clearance = 26 mL/min/kg

Comparative Example (Example I in WO2011/021038)

The following protocol was used to determine oral bio-availability and clearance, and the results are shown below:
Species=male mouse;
Strain=CD1;
n=3 male mice per time point per route;
Terminal blood sampling at 8 time points (5 min, 10 min, 0.5 hr, 1 hr, 3 hr, 6 hr, 8 hr and, 24 hr);
Collection of plasma, bio-analysis and report of AUC, AUMC, Vss, CL, half-life, MRT and bioavailability.
Formulation: 10% DMSO, 90% Saline
Dosing: 10 mg/kg P.O. and 5 mg/kg I.V.
Plasma PK Summary:

| Parameters - IV, 5 mg/kg | Value - Mesylate Salt | Value - HCl Salt |
|---|---|---|
| $t_{1/2}$ (hr) | 1.6 | 7.6 |
| $T_{max}$ (hr) | 0.08 | 0.08 |
| $C_{max}$ (ng/mL) | 1618 | 1712 |
| $AUC_{last}$ (hr*ng · mL) | 1245 | 1479 |
| $AUC_{all}$ (hr*ng/mL) | 1245 | 1479 |
| $AUC_{inf}$ (hr*ng/mL) | 1261 | 1515 |
| Clearance (mL/hr/Kg) | 3966 | 3300 |
| Vd (mL/Kg) | 4601 | 10063 |

| Parameters - PO, 10 mg/kg | Value - Mesylate Salt | Value - HCl Salt |
|---|---|---|
| $t_{1/2}$ (hr) | 1.9 | 1.8 |
| $T_{max}$ (hr) | 1.0 | 1.0 |
| $C_{max}$ (ng/mL) | 212 | 322 |
| $AUC_{last}$ (hr*ng/mL) | 657 | 849 |
| $AUC_{all}$ (hr*ng/mL) | 657 | 849 |
| $AUC_{inf}$ (hr* ng/mL) | 700 | 896 |
| F | 27.8% | 29.6% |

Example I in WO2011/021038 (Comparative)

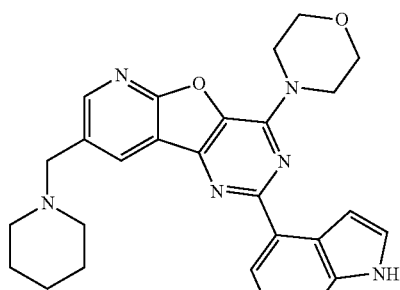

Oral bioavailability (F) = 28%
Clearance = 66 mL/min/kg

SUMMARY

| Compound | Oral Bioavailability (F) | Clearance (mL/min/kg) |
|---|---|---|
| Example A | 74 | 21 |
| Example B | 74 | 33 |
| Example G | 30 | 26 |
| Example I from WO2011/021038 (comparative) | 28 | 66 |

The invention claimed is:

1. A pharmaceutical composition comprising a compound represented by:

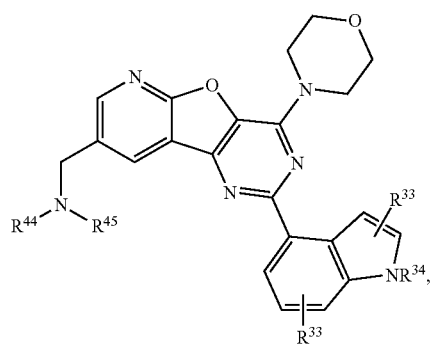

or a pharmaceutically acceptable salt thereof, and a pharmaceutically acceptable excipient, wherein:
$R_{33}$ is independently selected for each occurrence from the group consisting of H, halogen, NH—$C_{1-3}$alkyl, $NH_2$, $C_{1-6}$alkyl and —O—$C_{1-6}$alkyl, wherein $C_{1-6}$alkyl for each occurrence is optionally substituted by one, two or three substituents selected from halogen or hydroxyl;
$R^{34}$ is selected from H or $C_{1-3}$alkyl; and
$R^{44}$ and $R^{45}$, when taken together with the nitrogen to which they are attached form a 7-10 membered bicyclic spirocycle or bridged heterocycle each having an additional heteroatom selected from the group consisting of O, S, and $NR^{55}$, wherein $R^{55}$ is H or $C_{1-3}$alkyl.

2. The pharmaceutical composition of claim 1, wherein $R^{44}$ and $R^{45}$, when taken together with the nitrogen to which they are attached form a 7-8 membered bicyclic bridged heterocycle represented by:

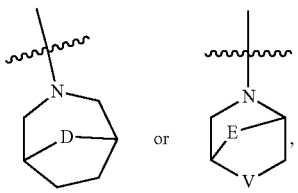

wherein:
D is selected from the group consisting of O, S and $NR^{55}$;
E is $(CH_2)_r$, wherein r is 1 or 2,
V is O or $NR^{55}$, and
$R^{55}$ is H or $C_{1-3}$alkyl.

3. The pharmaceutical composition of claim 1, wherein $R^{44}$ and $R^{45}$, when taken together with the nitrogen to which they are attached form a 7-10 membered spirocycle having one additional heteroatom selected from O or $NR^{55}$, wherein $R^{55}$ is H or $C_{1-3}$alkyl.

4. A compound represented by:

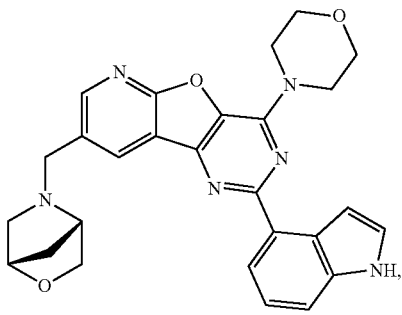 [SMILES: c1cc(-c2nc(N3CCOCC3)c3oc4ncc(CN5C[C@@H]6C[C@H]5CO6)cc4c3n2)c2cc[nH]c2c1]

or a pharmaceutically acceptable salt thereof.

5. A pharmaceutical composition comprising the compound of claim 4, or a pharmaceutically acceptable salt thereof, and a pharmaceutically acceptable excipient.

6. A method of treating a cancer in a patient in need thereof, wherein the cancer is selected from the group consisting of a leukaemia, lymphoma, solid tumour, and PTEN-negative tumour, the method comprising administering to the patient a therapeutically effective amount of a compound represented by:

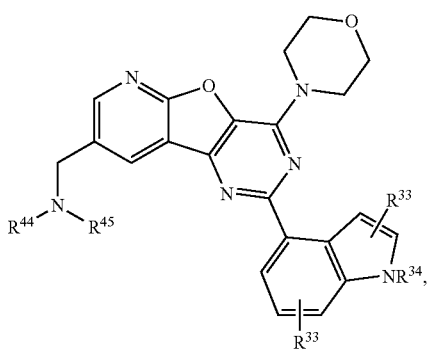

or a pharmaceutically acceptable salt thereof, wherein:
   $R_{33}$ is independently selected for each occurrence from the group consisting of H, halogen, NH—$C_{1-3}$alkyl, $NH_2$, $C_{1-6}$alkyl and —O—$C_{1-6}$alkyl, wherein $C_{1-6}$alkyl for each occurrence is optionally substituted by one, two or three substituents selected from halogen or hydroxyl;
   $R^{34}$ is selected from H or $C_{1-3}$alkyl; and
   $R^{44}$ and $R^{45}$, when taken together with the nitrogen to which they are attached form a 7-10 membered bicyclic spirocycle or bridged heterocycle each having an additional heteroatom selected from the group consisting of O, S, and $NR^{55}$, wherein $R^{55}$ is H or $C_{1-3}$alkyl.

7. The method of claim 6, wherein $R^{44}$ and $R^{45}$, when taken together with the nitrogen to which they are attached form a 7-8 membered bicyclic bridged heterocycle represented by:

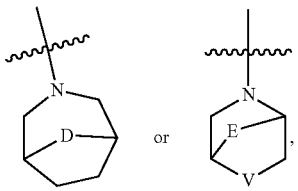

wherein:
   D is selected from the group consisting of O, S and $NR^{55}$;
   E is $(CH_2)_r$, wherein r is 1 or 2,
   V is O or $NR^{55}$, and
   $R^{55}$ is H or $C_{1-3}$alkyl.

8. The method of claim 6, wherein $R^{44}$ and $R^{45}$, when taken together with the nitrogen to which they are attached form a 7-10 membered spirocycle having one additional heteroatom selected from O or $NR^{55}$, wherein $R^{55}$ is H or $C_{1-3}$alkyl.

9. The method of claim 6, wherein the compound is:

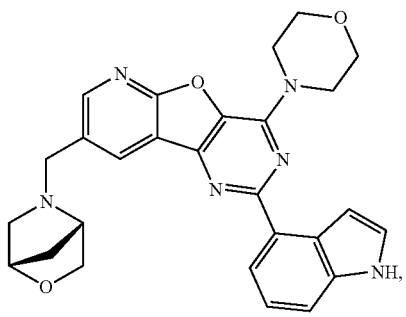 [SMILES: c1cc(-c2nc(N3CCOCC3)c3oc4ncc(CN5C[C@@H]6C[C@H]5CO6)cc4c3n2)c2cc[nH]c2c1]

or a pharmaceutically acceptable salt thereof.

10. The method of claim 6, wherein the PTEN-negative tumor is selected from the group consisting of PTEN-negative haematological, breast, lung, endometrial, skin, brain and prostate cancers.

11. The method of claim 6, wherein the cancer is leukaemia or lymphoma.

* * * * *